US012758794B2

(12) United States Patent
Timmerman et al.

(10) Patent No.: US 12,758,794 B2
(45) Date of Patent: Oct. 13, 2026

(54) PERSONALIZED ULTRA-FRACTIONATED STEREOTACTIC ADAPTIVE RADIOTHERAPY

(71) Applicant: The Board of Regents of The University of Texas System, Austin, TX (US)

(72) Inventors: Robert Timmerman, Westlake, TX (US); Debabrata Saha, Carrollton, TX (US); Michael D. Story, Dallas, TX (US); Hak Choy, Dallas, TX (US); Steve Bin Jiang, Southlake, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 1078 days.

(21) Appl. No.: 17/753,038

(22) PCT Filed: Sep. 14, 2020

(86) PCT No.: PCT/US2020/050745
§ 371 (c)(1),
(2) Date: Feb. 16, 2022

(87) PCT Pub. No.: WO2021/051089
PCT Pub. Date: Mar. 18, 2021

(65) Prior Publication Data
US 2022/0355128 A1 Nov. 10, 2022

Related U.S. Application Data

(60) Provisional application No. 62/900,166, filed on Sep. 13, 2019.

(51) Int. Cl.
*A61N 5/10* (2006.01)

(52) U.S. Cl.
CPC ......... *A61N 5/1038* (2013.01); *A61N 5/1039* (2013.01); *A61N 2005/1098* (2013.01)

(58) Field of Classification Search
None
See application file for complete search history.

(56) References Cited

U.S. PATENT DOCUMENTS 6,868,289 B2 3/2005 Palti
7,016,725 B2 3/2006 Palti
(Continued)

FOREIGN PATENT DOCUMENTS

TW 201136934 A 11/2011
WO 2009117484 A2 9/2009
(Continued)

OTHER PUBLICATIONS

Selleck, RGB-286638 free base, 2022, 3 pages, https://www.selleckchem.com/products/rgb-286638-free-base.html.
(Continued)

*Primary Examiner* — Thaddeus B Cox
(74) *Attorney, Agent, or Firm* — NORTON ROSE FULBRIGHT US LLP

(57) ABSTRACT

In one aspect, the present disclosure relates to a method of adaptive treatment of a subject with a tumor. The method may include administering a first pulse dose of radiation to a tumor within a subject; administering a second pulse dose of radiation to the tumor, wherein the second pulse dose is administered after an observation period, the observation period having a duration of at least 7 days; and concurrently treating the subject with an immunotherapy.

19 Claims, 15 Drawing Sheets

(56) References Cited

U.S. PATENT DOCUMENTS

| | | | |
|---|---|---|---|
| 7,089,054 | B2 | 8/2006 | Palti |
| 7,136,699 | B2 | 11/2006 | Palti |
| 7,146,210 | B2 | 12/2006 | Palti |
| 7,333,852 | B2 | 2/2008 | Palti |
| 7,467,011 | B2 | 12/2008 | Palti |
| 7,519,420 | B2 | 4/2009 | Palti |
| 7,565,205 | B2 | 7/2009 | Palti |
| 7,565,206 | B2 | 7/2009 | Palti |
| 7,599,745 | B2 | 10/2009 | Palti |
| 7,599,746 | B2 | 10/2009 | Palti |
| 7,706,890 | B2 | 4/2010 | Palti |
| 7,715,921 | B2 | 5/2010 | Palti |
| 7,805,201 | B2 | 9/2010 | Palti |
| 7,890,183 | B2 | 2/2011 | Palti et al. |
| 7,912,540 | B2 | 3/2011 | Palti |
| 7,917,227 | B2 | 3/2011 | Palti |
| 8,019,414 | B2 | 9/2011 | Palti |
| 8,027,738 | B2 | 9/2011 | Palti |
| 8,170,684 | B2 | 5/2012 | Palti |
| 8,175,698 | B2 | 5/2012 | Palti et al. |
| 8,229,555 | B2 | 7/2012 | Palti |
| RE43,618 | E | 8/2012 | Palti |
| 8,244,345 | B2 | 8/2012 | Palti |
| 8,406,870 | B2 | 3/2013 | Palti |
| 8,447,395 | B2 | 5/2013 | Palti et al. |
| 8,447,396 | B2 | 5/2013 | Palti et al. |
| 8,465,533 | B2 | 6/2013 | Palti |
| 8,706,261 | B2 | 4/2014 | Palti |
| 8,715,203 | B2 | 5/2014 | Palti |
| 8,718,756 | B2 | 5/2014 | Palti |
| 8,764,675 | B2 | 7/2014 | Palti |
| 9,023,090 | B2 | 5/2015 | Palti |
| 9,023,091 | B2 | 5/2015 | Palti |
| 9,039,674 | B2 | 5/2015 | Palti et al. |
| 9,056,203 | B2 | 6/2015 | Palti et al. |
| 9,440,068 | B2 | 9/2016 | Palti et al. |
| 9,655,669 | B2 | 5/2017 | Palti et al. |
| 9,750,934 | B2 | 9/2017 | Palti et al. |
| 10,188,851 | B2 | 1/2019 | Wenger et al. |
| 2007/0239213 | A1 | 10/2007 | Palti |
| 2011/0053977 | A1 | 3/2011 | Cress et al. |
| 2012/0035244 | A1 | 2/2012 | Chinnaiyan et al. |
| 2016/0129282 | A1 | 5/2016 | Mn et al. |
| 2017/0093277 | A1 | 3/2017 | Wasserman et al. |
| 2017/0209579 | A1 | 7/2017 | Curley et al. |
| 2017/0215939 | A1 | 8/2017 | Palti et al. |
| 2017/0281934 | A1 | 10/2017 | Giladi et al. |
| 2017/0319256 | A1 | 11/2017 | Kang et al. |
| 2018/0001075 | A1 | 1/2018 | Kirson et al. |
| 2018/0001078 | A1 | 1/2018 | Kirson et al. |
| 2018/0008708 | A1 | 1/2018 | Giladi et al. |
| 2018/0050200 | A1 | 2/2018 | Wasserman et al. |
| 2018/0160933 | A1 | 6/2018 | Urman et al. |
| 2018/0202991 | A1 | 7/2018 | Giladi et al. |
| 2019/0022411 | A1 | 1/2019 | Parry et al. |
| 2019/0298982 | A1 | 10/2019 | Story et al. |
| 2019/0307781 | A1 | 10/2019 | Krex et al. |
| 2019/0345566 | A1 | 11/2019 | Khera et al. |
| 2020/0297286 | A1 | 9/2020 | Costa et al. |
| 2021/0027878 | A1* | 1/2021 | He ........................ G16H 50/70 |
| 2021/0292741 | A1 | 9/2021 | Story et al. |
| 2023/0347173 | A1 | 11/2023 | Story et al. |

FOREIGN PATENT DOCUMENTS

| | | | |
|---|---|---|---|
| WO | 2011101417 | A1 | 8/2011 |
| WO | 2012146936 | A1 | 11/2012 |
| WO | 2013071415 | A1 | 5/2013 |
| WO | 2019025440 | A1 | 2/2019 |
| WO | 2019075391 | A1 | 4/2019 |
| WO | 2019238873 | A1 | 12/2019 |
| WO | 2020160213 | A1 | 8/2020 |
| WO | 2021051089 | A1 | 3/2021 |

OTHER PUBLICATIONS

Sirbu B.M., et al., "Analysis of Protein Dynamics at Active, Stalled, and Collapsed Replication Forks," Genes Development, 2011, vol. 25, pp. 1320-1327.

Sishc B.J., "Telomeres and Telomerase in the Radiation Response: Implications for Instability, Reprograming, and Carcinogenesis," Frontiers in Oncology, Nov. 24, 2015, vol. 5, No. 257, 19 pages.

Stupp R., et al., "Maintenance Therapy With Tumor-Treating Fields plus Temozolomide vs Temozolomide Alone for Glioblastoma: A Randomized Clinical Trial," JAMA, Dec. 15, 2015, vol. 314, No. 23, pp. 2535-2543.

Su F., et al., "Replication Stress Induced Site-Specific Phosphorylation Targets WRN to the Ubiquitin-Proteasome Pathway," Oncotarget, Dec. 18, 2015, vol. 7, No. 1, 20 pages.

Turner N., et al., "Hallmarks of 'BRCAness' in Sporadic Cancers," Nature Reviews Cancer, Oct. 2004, vol. 4, pp. 1-6.

Ulukan H., et al., "Camptothecins: A Review of their Chemotherapeutic Potential," Drugs, 2002, vol. 62, No. 14, pp. 2039-2057.

Venere M., et al., "Phosphorylation of ATR-Interacting Protein on Ser239 Mediates an Interaction with Breast-Ovarian Cancer Susceptibility 1 and Checkpoint Function," Cancer Research, Jul. 1, 2007, vol. 67, No. 13, pp. 6100-6105.

Voloshin T., et al., "Alternating Electric Fields (TTfields) In Combination with Paclitaxel are Therapeutically Effective Against Ovarian Cancer Cells in Vitro and In Vivo," International Journal of Cancer, 2016, vol. 139, pp. 2850-2858.

Vymazal J., et al., "Response Patterns of Recurrent Glioblastomas Treated with Tumor-Treating Fields," Seminars in Oncology, Oct. 2014, vol. 41, No. 5, Supplement 6, pp. S14-S24, 25 Pages.

Wallez Y., et al., "The ATR Inhibitor AZD6738 Synergizes with Gemcitabine In Vitro and In Vivo to Induce Pancreatic Ductal Adenocarcinoma Regression," Molecular Cancer Therapeutics, Aug. 2018, vol. 17, No. 8, pp. 1670-1682.

Wenger C., et al., "Modeling Tumor Treating Fields (TTFields) Application in Single Cells During Metaphase and Telophase," Conference Proceedings : Annual International Conference of the IEEE Engineering in Medicine and Biology Society IEEE Engineering in Medicine and Biology Society Annual Conference, 2015, pp. 6892-6895.

Wong E.T., et al., "Response Assessment of NovoTTF-100A Versus Best Physician's Choice Chemotherapy in Recurrent Glioblastoma," Cancer Medicine, 2014, vol. 3, 11 Pages.

Yuan K., et al., "Selective Inhibition of CDK4/6: A Safe and Effective Strategy for Developing Anticancer Drugs," Acta Pharmaceutica SInica B, 2021, vol. 11 (1), pp. 30-54.

Zhang J., et al., "Targeting DNA Replication Stress for Cancer Therapy," Genes (Basel), Aug. 19, 2016, vol. 7, 16 Pages.

Cavanagh H., et al., "The role of BRCA1 and BRCA2 Mutations in Prostate, Pancreatic and Stomach Cancers," Hereditary Cancer in Clinical Practice, 2015, vol. 13, No. 16, 8 pages.

Cescutti R., et al., "TopBP1 Functions With 53BP1 in the G1 DNA Damage Checkpoint," The EMBO Journal, 2010, vol. 29, No. 21, pp. 3723-3732.

Chan K.L., et al., "Replication Stress Induces Sister-Chromatid Bridging at Fragile Site Loci in Mitosis," Nature Cell Biology, Jun. 2009, vol. 11, No. 6, pp. 753-775.

Das A.K., et al., "Non-Small-Cell Lung Cancers with Kinase Domain Mutations in the Epidermal Growth Factor Receptor are Sensitive to Ionizing Radiation," Cancer Research, Oct. 2006, vol. 66, No. 19, pp. 9601-9608.

Davies A.M., et al., "Tumor Treating Fields: A New Frontier in Cancer Therapy," Annals of the New York Academy of Sciences, 2013, vol. 1291, pp. 86-95.

Dillon M.T., et al., "PATRIOT: A Phase I Study to Assess the Tolerability, Safety and Biological Effects of a Specific Ataxia Telangiectasia and Rad3-Related (ATR) Inhibitor (AZD6738) as a Single Agent and in Combination with Palliative Radiation Therapy in Patients with Solid Tumours," Clinical and Translational Radiation Oncology, 2018, vol. 12, 5 Pages.

Ding L., et al., "Enhanced Identification and Biological Validation of Differential Gene Expression via Illumina Whole-Genome Expres-

(56) References Cited

OTHER PUBLICATIONS sion Arrays Through The Use of the Model-Based Background Correction Methodology," Nucleic Acids Research, 2008, vol. 36, No. 10, p. e58, 10 pages.
Examination and Search Report of Taiwan Patent Application No. 110110392, (from The Tai E International Patent Law Office), dated Dec. 13, 2021, 10 Pages.
Foucquier J., et al., "Analysis of Drug Combinations: Current Methodological Landscape," Pharmacology Research Perspectives, 2015, vol. 3, No. 3, p. e00149, 11 pages.
Franciosi V., et al., "Front-Line Chemotherapy with Cisplatin and Etoposide for Patients with Brain Metastases from Breast Carcinoma, Nonsmall Cell Lung Carcinoma, or Malignant Melanoma," A Prospective Study, Cancer, Apr. 1, 1999, vol. 85, No. 7, 7 Pages.
Gaillard H., et al., "Replication Stress and Cancer," Nature Reviews, Cancer, May 2015, vol. 15, pp. 276-289.
Geary N., et al., "Understanding Synergy," American Journal of Physiology—Endocrinology and Metabolism, Dec. 4, 2012, vol. 304, pp. E237-E253, 67 pages.
Gera N., et al., "Tumor Treating Fields Perturb the Localization of Septins and Cause Aberrant Mitotic Exit," PLOS One, May 26, 2015, 20 pages.
Giladi M., et al., "Alternating Electric Fields (Tumor-Treating Fields Therapy) Can Improve Chemotherapy Treatment Efficacy in Non-Small Cell Lung Cancer Both In Vitro and In Vivo," Seminars in Oncology, Oct. 2014, vol. 41, No. 5, pp. S35-S41.
Giladi M., et al., "Mitotic Disruption And Reduced Clonogenicity of Pancreatic Cancer Cells in Vitro and in Vivo by Tumor Treating Fields," Pancreatology: Official Journal of the International Association of Pancreatology, 2014, vol. 14, pp. 54-63.
Giladi M., et al., "Mitotic Spindle Disruption by Alternating Electric Fields Leads to Improper Chromosome Segregation and Mitotic Catastrophe in Cancer Cells," Scientific Reports, Dec. 11, 2015, vol. 5, No. 1, pp. 1-16.
Gonzalez C.F., et al., "Harnessing Dielectric Forces for Separations of Cells, Fine Particles and Macromolecules," Journal of Chromatography A, Apr. 2005, vol. 1079, pp. 59-68.
Huyen Y., et al., "Methylated lysine 79 of Histone H3 Targets 53BP1 to DNA double-strand breaks," Nature, Nov. 18, 2004, vol. 432, pp. 406-411.
International Preliminary Report on Patentability for International Application No. PCT/US2020/050745, mailed Mar. 24, 2022, 8 Pages.
International Preliminary Report on Patentability for International Application No. PCT/US2021/023393, mailed Oct. 6, 2022, 5 Pages.
International Search Report and Written Opinion for Application No. PCT/US2023/65242, mailed on Oct. 3, 2023, 9 Pages.
International Search Report and Written Opinion for International Application No. PCT/US2021/023393, mailed Jun. 8, 2021, 6 Pages.
International Search Report and Written Opinion for International Application No. PCT/US2022/020024, mailed Sep. 9, 2022, 12 Pages.
Inui T., et al., "Case Report: A Non-small Cell Lung Cancer Patient Treated with GcMAF, Sonodynamic Therapy and Tumor Treating Fields," Anticancer Research, 2016, vol. 36, 4 Pages.
Kaelin W.G., "The Concept of Synthetic Lethality in the Context of Anticancer Therapy," Nature Reviews Cancer, Sep. 2005, vol. 5, pp. 689-698.
Kan C., et al., "BRCA1 Mutation: A Predictive Marker for Radiation Therapy?," International Journal of Radiation Oncology, Biology, Physics, Oct. 1, 2015, vol. 93, No. 2, pp. 281-293.
Karanam N.K., et al., "Tumor-Treating Fields Elicit a Conditional Vulnerability to Ionizing Radiation via the Downregulation of BRCA1 Signaling and Reduced DNA Double-Strand Break Repair Capacity in Non-Small Cell Lung Cancer Cell Lines," Cell Death and Disease, 2017, vol. 8, No. 3, Article No. e2711, 10 Pages.
Kent L.N., et al., "The Broken Cycle: E2F Dysfunction in Cancer," Nature, Jun. 2019, vol. 19, pp. 326-338.
Kim E.H., et al., "Biological Effect of an Alternating Electric Field on Cell Proliferation and Synergistic Antimitotic Effect in Combination with Ionizing Radiation," Oncotarget, Aug. 19, 2016, vol. 7, No. 8, pp. 62267-62279.
Kirson E.D., et al., "Alternating Electric fields (TTFields) Inhibit Metastatic Spread of Solid Tumors to the Lungs," Clinical Experimental Metastasis, Apr. 2009, vol. 26, pp. 633-640.
Kirson E.D., et al., "Chemotherapeutic Treatment Efficacy and Sensitivity are Increased by Adjuvant Alternating Electric Fields (TTFields)," BMC Medical Physics, Jan. 8, 2009, vol. 9, pp. 1-13.
Kirson E.D., et al., "Disruption of Cancer Cell Replication by Alternating Electric Fields," Cancer Research, May 1, 2004, vol. 64, 8 Pages.
Kirson et al., "Alternating electric fields arrest cell proliferation in animal tumor models and human brain tumors," PNAS, Jun. 2007, vol. 104, No. 24, pp. 10152-10157.
Knudsen E.S., et al., "Biological Specificity of CDK4/6 Inhibitors: Dose Response Relationship, in Vivo Signaling, and Composite Response Signature," Oncotarget, Jun. 10, 2017, vol. 8, No. 27, pp. 43678-43691.
Kurtyka C.A., et al., "E2F Inhibition Synergizes with Paclitaxel in Lung Cancer Cell Lines," PLOS One, May 15, 2014, vol. 9, Issue. 5, pp. 1-9.
Lehar J., et al., "Chemical Combination Effects Predict Connectivity in Biological Systems," Molecular Systems Biology, vol. 3, No. 80, 200Z, 14 pages.
Longley D.B., et al., "5-Fluorouracil: Mechanisms of Action and Clinical Strategies," Nature Reviews Cancer, May 2003, vol. 3, 9 Pages.
McPherson J.P., et al., "A Role for Brca1 in chromosome end maintenance," Human Molecular Genetics, Jan. 2006, vol. 15, No. 6, pp. 831-838.
Militello A.M., et al., "Mechanism of Action and Clinical Efficacy of CDK4/6 Inhibitors in BRCA-Mutated, Estrogen Receptor-Positive Breast Cancers: Case Report and Literature Review," Frontiers in Oncology, Aug. 13, 2019, vol. 9, pp. 1-7.
Morgensztern D., et al., "Best of the Month: A Roundup of Articles Published in Recent Months," Journal of Thoracic Oncology : Official Publication of the International Association for the Study of Lung Cancer, Aug. 2010, vol. 5, No. 8, pp. 1305-1307.
Morgensztern D., et al., "Vaccines and Immunotherapy for Non-small Cell Lung Cancer," Journal of Thoracic Oncology : Official Publication of the International Association for the Study of Lung Cancer, Dec. 2010, vol. 5, No. 12, Supplement 6, 3 Pages.
Office Action and Search Report from Taiwan Patent Application No. 110110392, dated Oct. 24, 2023, 26 Pages.
Patel K.J., et al., "Involvement of Brca2 in DNA Repair," Molecular Cell, Feb. 1998, vol. 1, pp. 347-357.
Phillips R.J., et al., "Epidermal Growth Factor and Hypoxia-induced Expression of CXC Chemokine Receptor 4 on Non-small Cell Lung Cancer Cells Is Regulated by the Phosphatidylinositol Kinase/PTEN/AKT/mammalian Target of Rapamycin Signaling Pathway and Activation of Hypoxia Inducible Factor-1alpha," The Journal of Biological Chemistry, Jun. 10, 2005, vol. 280, No. 23, pp. 22473-22481.
Piezzo M., et al., "Targeting Cell Cycle in Breast Cancer: CDK4/6 Inhibitors," International Journal of Molecular Sciences, Sep. 4, 2020, vol. 21, pp. 1-23.
Pommier Y., et al., "DNA Topoisomerases and their Poisoning by Anticancer and Antibacterial Drugs," Chemistry and Biology, May 28, 2010, vol. 17, pp. 421-433, 26 Pages.
Roy R., et al., "BRCA1 and BRCA2: Different Roles in a Common Pathway of Genome Protection," Nature Reviews Cancer, Jan. 2012, vol. 12, No. 1, pp. 68-78.
Schlacher K., et al., "A Distinct Replication Fork Protection Pathway Connects Fanconi Anemia Tumor Suppressors to RAD51-BRCA 1/2," Cancer Cell, Jul. 10, 2012, vol. 22, pp. 106-116.
Schneiderman R.S., et al., "TTfields Alone and In Combination with Chemotherapeutic Agents Effectively Reduce the Viability of MDR Cell Sub-Lines That Over-Express ABC Transporters," BMC Cancer, 2010, vol. 10, No. 229, 28 pages.

(56) References Cited

OTHER PUBLICATIONS

Schultz et al., "p53 Binding Protein 1 (53bp1) is an Early Participant in the Cellular Response to DNA Double-Strand Breaks," The Journal of Cell Biology, Dec. 25, 2000, vol. 151, No. 7, pp. 1381-1390.
Extended European Search Report for Application No. 21774257.6, dated Mar. 20, 2024, 10 Pages.
Hoyer M., et al., "The Evolution of Radiotherapy Techniques in the Management of prostate Cancer," Acta Oncologica, May 14, 2015, vol. 54, 5 Pages.
Mun E J., et al., "Tumor-treating Fields: a Fourth Modality in Cancer Treatment," Clinical Cancer Research, Jan. 15, 2018, vol. 24, No. 2, 10 Pages.
Office Action from Taiwan Patent Application No. 110110392, dated May 10, 2024, 5 Pages.
PCT International Application No. PCT/US20/50745, International Search Report and Written Opinion of the International Searching Authority, dated Dec. 7, 2020, 6 pages.
Karanam N.K., et al., "Tumor Treating Fields Cause Replication Stress and Interfere with DNA Replication Fork Maintenance: Implications for Cancer Therapy," Translational Research, 2020, vol. 217, pp. 33-46.
Naz S., et al., "Abemaciclib, a Selective CDK4/6 Inhibitor, Enhances the Radiosensitivity of Non-Small Cell Lung Cancer In Vitro and In Vivo," Clinical Cancer Research, 2018, vol. 24, vol. 16, pp. 3994-4005.
Office Action for European Patent Application No. 21774257.6, mailed Oct. 29, 2025, 7 pages.
Office Action for Japanese Patent Application No. 2022-558097, mailed Nov. 4, 2025, 4 pages.
Office Action for Japanese Patent Application No. 2022-558097, mailed May 20, 2025, 12 pages.
Patnaik A., et al., "Efficacy and Safety of Abemaciclib, an Inhibitor of CDK4 and CDK6, for Patients with Breast Cancer, Non-Small Cell Lung Cancer, and Other Solid Tumors," Cancer Discovery, 2016, vol. 6, No. 7, pp. 740-753.

* cited by examiner

PERSONALIZED ULTRA-FRACTIONATED STEREOTACTIC ADAPTIVE RADIOTHERAPY

CROSS-REFERENCE TO RELATED APPLICATIONS

This application is a National Stage of PCT/US2020/050745, filed Sep. 14, 2020, which claims the benefit of U.S. Provisional Application Ser. No. 62/900,166, filed Sep. 13, 2019, which are incorporated by reference in their entireties.

BACKGROUND

Conventional techniques of radiotherapy treatment for cancer patients have almost exclusively been restricted to fractionated doses of radiation. Fractionated doses, or fractions, are administered within a short time frame, on consecutive days, or even multiple times per day or every other day, over the course of a few weeks. This is known as conventional fractionated radiotherapy (CFRT). In this timeframe, a patient would receive daily or near-daily doses of radiation. The radiation is typically administered with a linear accelerator and is used to control or kill malignant cells that make up a tumor.

Various attempts at applying split-course treatments of radiotherapy have been attempted, but never to the point of success. Split-course treatment is an intentional separation or spreading out of radiation doses. In the past, the split or rest period occurred between clusters of fractionated doses, e.g., at the half-way point of a 6 week course, a 1-4 week break with no therapy was inserted. Historically, the motivation for this was to reduce toxicity, allowing more time for the normal tissue surrounding the tumor to heal from what would otherwise be a difficult and toxic long course of radiation. However, tumor control penalties caused by tumor proliferation plagued these attempts, meaning that, with the extra time between doses, the tumor would begin to grow back.

As a result, radiotherapy treatments in general tend to be very rigid and do not allow for much adaptation or personalization. It is not uncommon for the only customization in radiotherapies to be based on the type and location of the tumor determined prior to the onset of therapy. For example, a patient with primary lung cancer may be put on a treatment sequence consisting of 30 fractions of 2 Gy (Gray) over 6 weeks, while a patient with metastatic kidney cancer may receive 5 fractions of 8 Gy every other day over 2 weeks. However, there is little customization or adaptation, such as narrowing the radiation field because of a shrinkage in tumor size, beyond that. Since little real change occurs throughout the course of conventional therapy, the entire course is planned prior to the start of all therapy and executed without modification or adaptation. Because of this rigidity, there can be a tendency for patients to be either over- or under-treated. Furthermore, even if adaptation is implemented, there is little time for the tumor or its environment to demonstrate notable or noticeable changes that might influence adaptations or personalizations with such a short amount of time between fractions and completion of all radiotherapy typically within 4-6 weeks total.

SUMMARY

Embodiments of the present disclosure relate to methods for providing adaptive treatment of a subject with a tumor. According to one aspect of the present disclosure, the method may include administering a first pulse dose of radiation to a tumor within a subject; administering a second pulse dose of radiation to the tumor, wherein the second pulse dose is administered after an observation period, the observation period having a duration of at least 7 days; and concurrently treating the subject with an immunotherapy. In some embodiments, the first and second pulse doses of radiation may be ablative.

In some embodiments, the first and second pulse doses may be part of a radiotherapy, the radiotherapy may include stereotactic ablative radiotherapy (SABR). In some embodiments, concurrently treating the subject with the immunotherapy may include administering an immune stimulant with at least one pulse dose of radiation. In some embodiments, the immune stimulant may include at least one of a checkpoint inhibitor, an immune stimulating cytokine, a tumor derived immune stimulant, or an agent associated with the cGAS STING pathway. In some embodiments, in response to administering the first pulse dose, the method may include determining at least one of a level of radiation for the second pulse dose, the duration of the observation period, and a target field for the second pulse dose using a machine learning model.

In some embodiments, determining at least one of a level of radiation for the second pulse dose, the duration of the observation period, and a target field for the second pulse dose using a machine learning model may include training the machine learning model to analyze radiomic features and biologic features. In some embodiments, biologic features may include at least one of target tissue vascularity, normal tissue vascularity, target tissue oxygenation status, normal tissue oxygenation status, target tissue cytokine profile, normal tissue cytokine profile, target tissue gene expression, normal tissue gene expression, circulating tumor DNA indicative of tumor response to therapy, the levels of circulating tumor cells, target tissue receptor expression, normal tissue receptor expression, target tissue white blood cell infiltration, normal tissue white blood cell infiltration, tumor markers, tumor burden, systemic immune status, changes in subject health, and changes in patient weight.

In some embodiments, radiomic features may include at least one anatomical imaging characteristics, functional imaging characteristics, and metabolic imaging characteristics. In some embodiments, the tumor may be one of a benign tumor and a malignant tumor. In some embodiments, the first pulse dose may be at least 6 Gy. In some embodiments, the second pulse dose may be between 15 Gy and 50 Gy.

According to another aspect of the present disclosure, a method may include administering a first pulse dose of radiation to a tumor within a subject; concurrently treating the subject with an immunotherapy; measuring biologic features of at least one of the subject and the tumor; applying at least one medical imaging technique to at least one of the subject and the tumor; analyzing results of the at least one medical imaging technique and the biologic features with a machine learning model; determining, based on the analysis with the machine learning model, at least one of a level of radiation for a second pulse dose, a duration between the first dose and the second pulse dose, and a target field for the second pulse dose; and administering the second pulse dose, wherein the second pulse dose is administered at least 7 days after the first pulse dose.

In some embodiments, the first and second pulse doses may be ablative. In some embodiments, the biologic features may include at least one of target tissue vascularity, normal tissue vascularity, target tissue oxygenation status, normal tissue oxygenation status, target tissue cytokine profile, normal tissue cytokine profile, target tissue gene expression, normal tissue gene expression, circulating tumor DNA indicative of tumor response to therapy, the levels of circulating tumor cells target tissue receptor expression, normal tissue receptor expression, target tissue white blood cell infiltration, normal tissue white blood cell infiltration, tumor markers, tumor burden, systemic immune status, changes in subject health, and changes in patient weight.

In some embodiments, performing imaging may include at least one of anatomical imaging, functional imaging, and metabolic imaging. In some embodiments, concurrently treating the subject with the immunotherapy may include administering an immune stimulant with at least one pulse dose of radiation. In some embodiments, the immune stimulant may include a checkpoint inhibitor, an immune stimulating cytokine, a tumor derived immune stimulant, and an agent associated with the cGAS STING pathway. In some embodiments, the first and second pulse doses may be part of a radiotherapy, the radiotherapy including stereotactic ablative radiotherapy (SABR).

According to yet another aspect of the present disclosure, a method may include administering a first pulse dose of radiation to a tumor within a subject; measuring biologic features of at least one of the subject and the tumor; applying at least one medical imaging technique to at least one of the subject and the tumor; analyzing results of the at least one medical imaging technique and the biologic features with a machine learning model; determining, based on the analysis with the machine learning model, at least one of a level of radiation for a second pulse dose, a duration between the first pulse dose and the second pulse dose, and a target field for the second pulse dose; and administering the second pulse dose, wherein the second pulse dose is administered at least 7 days after the first pulse dose.

BRIEF DESCRIPTION OF THE DRAWINGS

Various objectives, features, and advantages of the disclosed subject matter can be more fully appreciated with reference to the following detailed description of the disclosed subject matter when considered in connection with the following drawings, in which like reference numerals identify like elements.

Figure 1A:
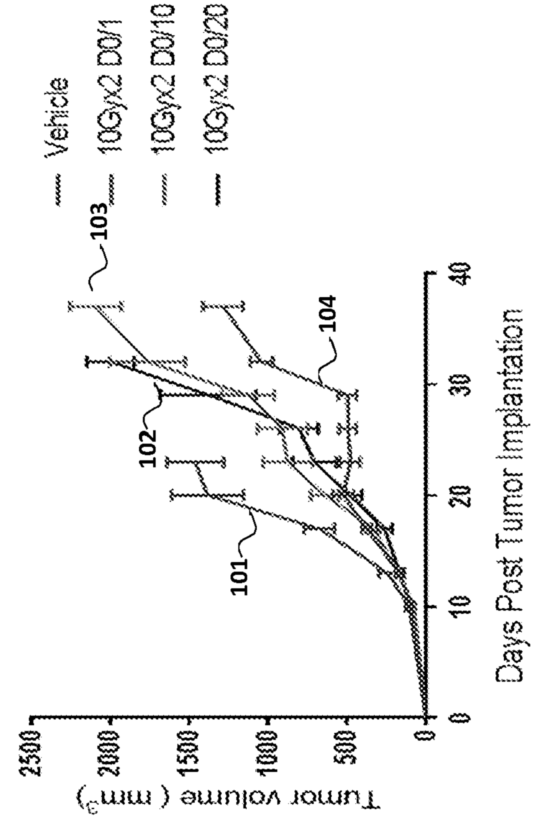
FIGS. 1A-1B show preclinical tumor responses for various dose levels of radiation as well as controlled, unirradiated animals treated only with a presumed inactive drug called the vehicle.

The drawings are not necessarily to scale, or inclusive of all elements of a system, emphasis instead generally being placed upon illustrating the concepts, structures, and techniques sought to be protected herein.

DETAILED DESCRIPTION

A recent development in radiotherapy for tumor treatment is stereotactic ablative radiotherapy (SABR). SABR has some similarities with CFRT in that it uses doses of targeted radiation to kill tumor cells. However, SABR employs much more potent doses or fractions of radiation, called ablative doses, sometimes up to 10 times the potency. This is facilitated mainly due to significant advancements in medical imaging technology, allowing fractions to be almost exclusively targeted toward the tumor with little to no normal tissue being affected. Implementations of SABR, though, have followed some of the customs of CFRT; e.g., SABR techniques are still typically given on similar schedules with fractions being administered daily or close to daily.

However, it has been discovered that the immediate response of a tumor to an ablative pulse of radiation, such as one in SABR, can be more extreme than expected. For example, the anatomical response, or shrinkage, can certainly be much greater with SABR than with CFRT. An ablative pulse may cause considerable damage to the DNA of the tumor, disrupting proliferation. It may also cause serious cell death through apoptosis or damage to the tumor's vasculature. The degree of response may be great enough that, in fact, the previous shortcomings of employing split-course treatments to tumors can be avoided (i.e., avoid the tumor control "penalty" manifesting as tumor proliferation during the break described in historical split course radiation experiences). In fact, limited experiences have been described where individual or clusters of SAbR doses have been split apart by more than the typical day or two with the goal of reducing toxicity as was previously done unsuccessfully with CFRT. However, there has been no previous attempt to use a split course of specifically SABR or SABR-like dosing with the goal of improving tumor control or cure. Indeed, all previous attempts to use split course dosing in the field of radiotherapy have led to the unfortunate result of decreasing tumor control or cure.

FIGS. 1-4 show preclinical tumor responses for various dose levels of radiation. This preclinical data was taken from a study using immune competent mice implanted in the hind flank with a murine tumor (Lewis lung carcinoma cells, which are importantly derived from the same mouse strain and can be referred to as LLC). This particular tumor is fast growing and radio-resistant. Tumor volume measurements are taken at multiple points in time. Typically, in real therapies outside of a laboratory environment, any growth of a tumor during radiotherapy constitutes the tumor control penalty. However, due to the extremely aggressive nature of Lewis lung carcinoma tumors in this laboratory model, a plateau in tumor volume (i.e. tumor neither grew nor shrunk) or, better, a decrease in tumor volume for any meaningful amount of time were both considered a success. When no plateau was witnessed throughout the duration of the experiment, i.e., the tumor continued to exhibit an upward growth trajectory despite the treatment, it was considered a penalty.

Some sets of trials and experiments include a vehicle trial. A vehicle refers to the antibody used in the same experiment for other trials but without the active receptor (i.e. it includes most of the antibody molecule but is missing the active receptor). This may serve as a control for the experiment, making sure that the receptor activity is what really causes the detected effects.

Figure 1B:
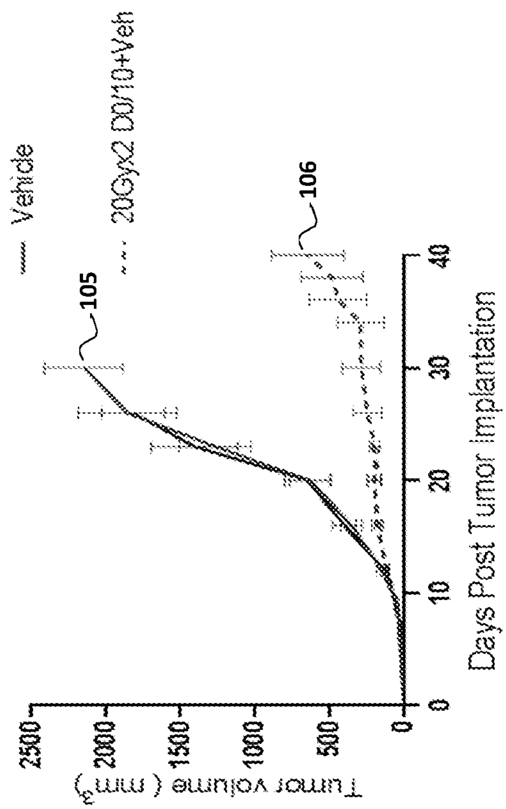

FIGS. 1A-1B show preclinical tumor responses for various dose levels of radiation separated (split) by variable numbers of days. FIG. 1A shows a preclinical plot of tumor volume over time. Line 101 corresponds to the vehicle. Line 104 corresponds to a treatment of 2 pulses of 10 Gy, separated by 1 day. Line 104 may be similar to a traditional SABR treatment because of the short duration between pulses. Line 103 corresponds to a treatment of 2 pulses of 10 Gy, separated by 10 days. Line 102 corresponds to a treatment of 2 pulses of 10 Gy with a separation of 20 days. Lines 102 and 103 may be similar to non-conventional, split-course SABR techniques because of the long duration between pulses. While treatment 104 separated by only a day (i.e., no split course) shows an expected beneficial temporary plateau of tumor control, all others show rapid, unrelenting growth. While this experiment did not assess whether toxicity was less with the longer intervals between treatments, it may be concluded that at the 10 Gy per treatment dose level for this particular animal/tumor model, a significant tumor control penalty exists with the split course treated animals.

FIG. 1B also shows a preclinical plot of tumor volume over time. Line 105 corresponds to a control vehicle. Line 106 is similar to a non-conventional, split-course SABR technique, like lines 102 and 103 of FIG. 1A. However, line 106 uses higher pulse doses of 20 Gy, separated by 10 days, rather than 10 Gy. Line 106, a treatment with double the potency of treatments in FIG. 1A, exhibits significantly decreased tumor growth, and, contrary to a plethora of historical split-course studies, does not constitute a tumor control penalty in the context of these experiments. Because of the near plateaued behavior up to around 35 days, this more potent SABR-like treatment can be considered to not exhibit the historically observed tumor control penalty.

Without the tumor proliferation penalty that historically occurred with long periods of time between fractions of radiation, there is now potential to use these time periods to allow the tumor and the patient's body to adapt to treatment changes to allow interrogation, modification, and optimization of subsequent treatment. This is called adaptation or personalization of therapy. By allowing the body and tumor to respond to an ablative dose of radiation over weeks or even months rather than just days, changes can be detected, analyzed, and used to tailor subsequent doses and adapt the remainder of the therapy. This can occur all while avoiding tumor proliferation (i.e., tumor control penalties) specifically if potent dose SABR or SABR-like split course dosing is employed rather than CFRT or even conventional daily or every other day SABR or SABR-like dosing used up to now. Adaptations to a radiotherapy may take into account many different types of data on the patient, and may warrant changes in the time between pulses, the potency of the pulses, and the target field of the radiation (i.e. how targeted the radiation is; a small target field would be used for a small tumor and vice versa). In addition, with the increase in time between pulses, this may facilitate the combination of other therapies, such as immunotherapy, chemotherapy, or targeted therapy, with the radiotherapy.

Figures 2A, 2B, 2C, 2D, 2E, 2F:
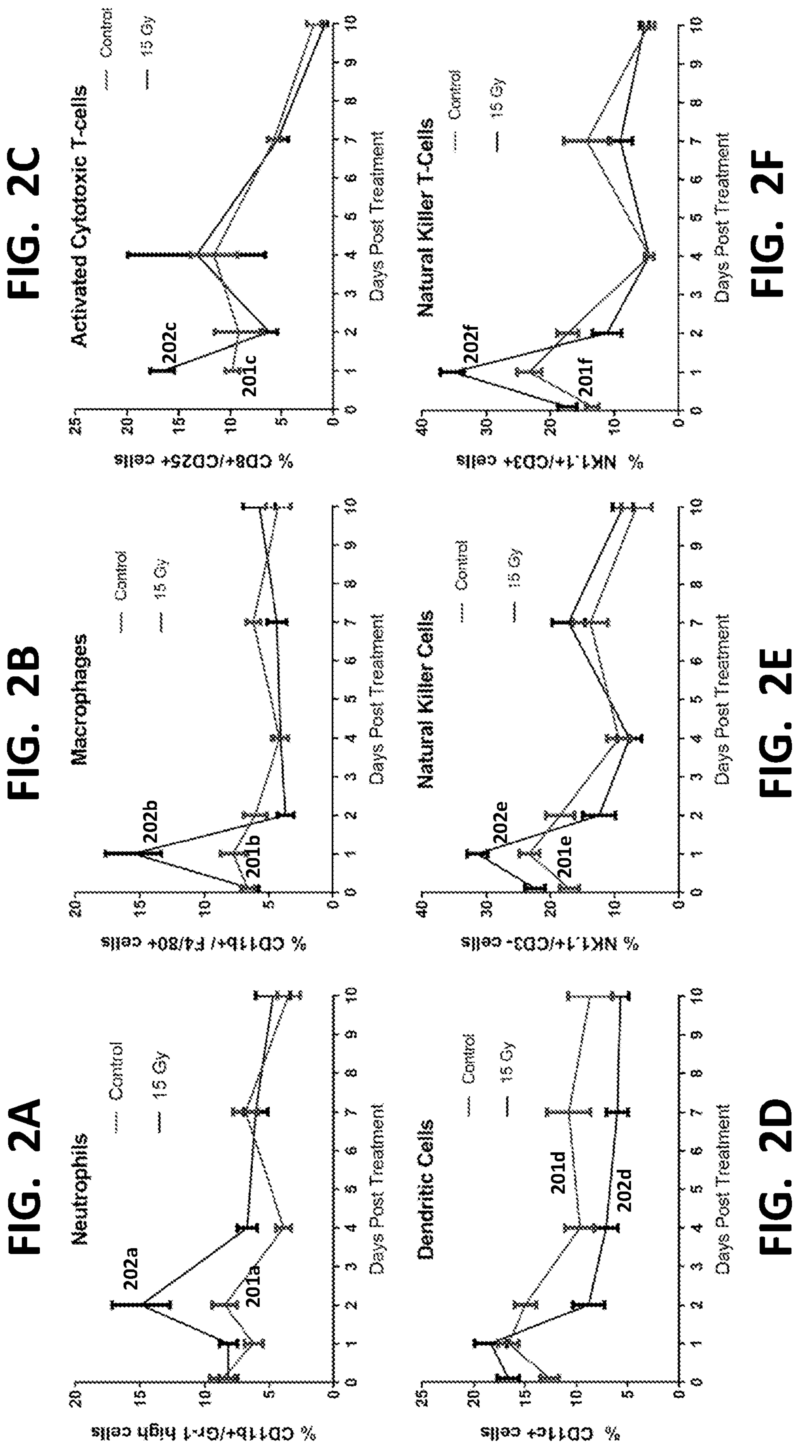
FIGS. 2A-2F show the timing of infiltrates into a tumor bed after an ablative dose of radiation.

FIGS. 2A-2F show the timing of infiltrates into a tumor bed after an ablative dose of radiation. In each of FIGS. 2A-2F, an ablative dose of radiation is given at day 0. FIG. 2A shows the infiltration of neutrophils, a type of white blood cell. FIG. 2B shows the infiltration of macrophages, a large phagocytic cell. FIG. 2C shows the infiltration of activated cytotoxic T-cells. FIG. 2D shows the infiltration of dendritic cells, or antigen-presenting cells. FIG. 2E shows the infiltration of natural killer cells. FIG. 2F shows in the infiltration of natural killer T-cells. Lines 201*a-f* correspond to a control group, where no radiation pulse was administered. Lines 202*a-f* correspond to a treatment where an ablative pulse of 15 Gy was administered at day 0. In FIGS. 2A-2F, where a pulse of radiation is administered, there is a noticeable spike in infiltration between 1-4 days after the treatment. However, all of these cells can be readily killed by even fairly low or moderate doses of radiation. This suggests that any radiotherapy techniques that administer radiation pulses daily or near-daily (i.e. CFRT, SABR, etc.) may actually result in immunosuppression. Furthermore, this also may suggest that split-course treatment with highly ablative doses of radiation, similar to those described in FIG. 1, may more optimally stimulate the immune system.

Figure 3A:
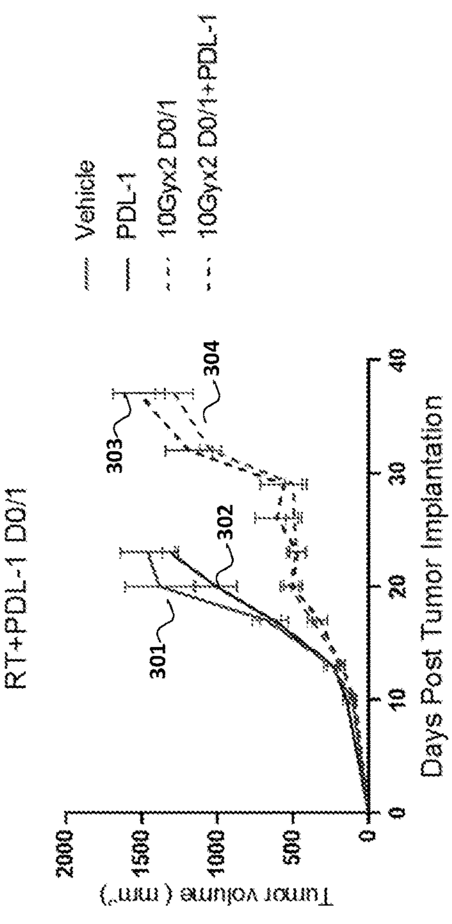
FIG. 3A-3B show preclinical tumor responses for various dose levels of radiation with an immune stimulating drug (PDL-1 antibody, vehicle is the antibody without the PDL-1 receptor serving as a control).
Figure 3B:
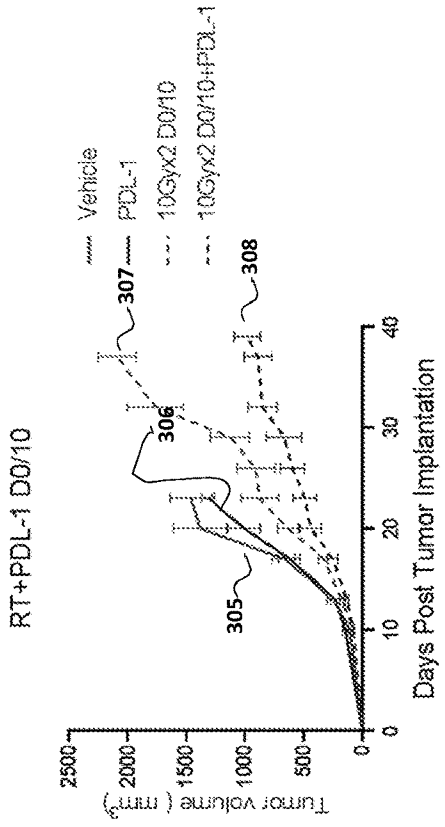

FIG. 3A-3B show preclinical tumor responses for various dose levels of radiation with an immune stimulating drug. FIG. 3A shows the change in tumor volume over time. Line 301 corresponds to a vehicle. Line 302 corresponds to a treatment that does not include radiation pulses but includes administering a dose of anti-PDL-1, an immune-stimulatory drug, referred to as simply PDL-1 in all figures. Line 304 corresponds to a treatment that includes administering 2 pulses of 10 Gy, separated by 1 day. Line 303 corresponds to a treatment that includes administering 2 pulses of 10 Gy, separated by 1 day, and at least one dose of anti-PDL-1. Lines 303 and 304 both exhibit a tumor growth plateau. There is also no meaningful difference between lines 303 and 304, suggesting that the addition of an immune-stimulatory drug did not have any effects. This may be because the second pulse was administered only one day after the initial pulse, killing the increased immune infiltration, as described in relation to FIG. 2. This may suggest the limitations of combining CFRT or conventional SABR techniques with immunotherapy using a daily treatment schedule.

FIG. 3B also shows change in tumor volume over time. Line 305 corresponds to a vehicle, and may be the same as line 301 of FIG. 3A. Line 306 corresponds to a treatment that does not include radiation pulses but includes administering a dose of anti-PDL-1, an immune-stimulatory drug, and may be the same as line 302 of FIG. 3A. Line 307 corresponds to a treatment that includes 2 pulses of 10 Gy, separated by 10 days. Line 308 corresponds to a treatment that includes 2 pulses of 10 Gy, separated by 10 days, and a dose of anti-PDL-1. Line 306 shows no improvement compared to the control, line 305, indicating the drug has no independent benefit. Line 308, where the 2nd pulse is not administered until 10 days after the initial dose, exhibits much lower tumor growth than the other treatments. This may suggest that the immune stimulation immediately after the initial dose, as described in relation to FIG. 2, was not suppressed by a second pulse as it was not administered until 10 days afterward. Line 303 of FIG. 3A (conventionally separated pulse combined with immunotherapy) had the tumor volume increase to nearly 1500 cubic mm by 40 days. On the other hand, line 308 of FIG. 3B (split-course pulse combined with radiotherapy) had the tumor volume increase to barely 1000 cubic mm by 40 days. This may be evidence that immunotherapy can be effective at improving tumor control when employed with ablative doses and a split course schedule but not with more conventional daily radiotherapy or when given alone.

Figure 4B:
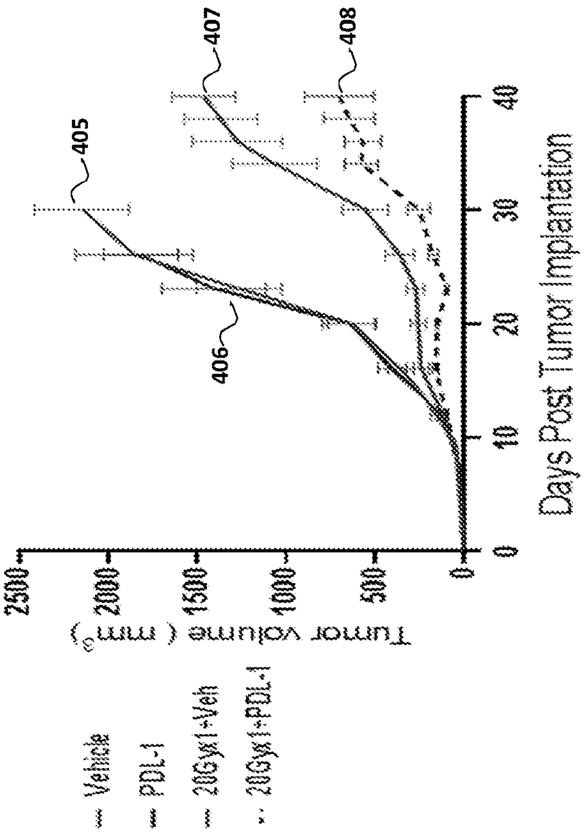
FIG. 4A-4B show further preclinical tumor responses for various dose levels of radiation with an immune stimulating drug.
Figure 4A:
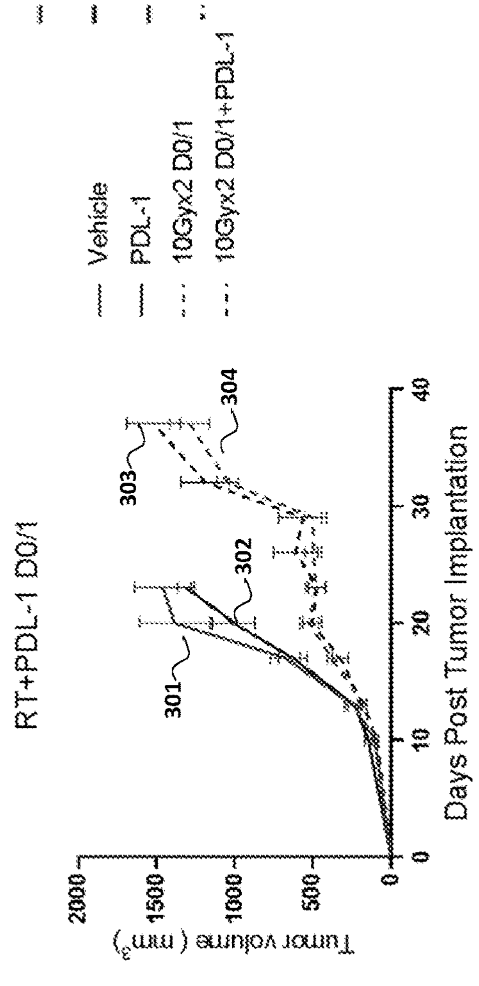

FIG. 4A-4B show further preclinical tumor responses for various dose levels of radiation with an immune stimulating drug. FIG. 4A is the same as FIG. 3A. Line 301 corresponds to a vehicle. Line 302 corresponds to a treatment that does not include radiation pulses but includes administering a dose of PDL-1, an immune-stimulatory drug. Line 304 corresponds to a treatment that includes administering two pulses of 10 Gy, separated by one day. Line 303 corresponds to a treatment that includes administering 2 pulses of 10 Gy, separated by one day, and a dose of PDL-1. Since lines 303 and 304 show no meaningful separation, it is concluded that immunotherapy given with a total of 20 Gy given as two 10 Gy doses separated by a single day is not effective at controlling this tumor model.

FIG. 4B also shows the change in tumor volume over time. Line 405 corresponds to a vehicle. Line 406 corresponds to a treatment that does not include radiation pulses but includes administering a dose of anti-PDL-1. Line 407 corresponds to a treatment that includes a single pulse of 20 Gy, i.e., 20 Gy given as a single 20 Gy dose rather than as two 10 Gy doses. Line 408 corresponds to a treatment that includes a single pulse of 20 Gy and a dose of anti-PDL-1. Line 408 has a very low tumor growth, only reaching a little over 500 cubic mm after 40 days, considerably better than the pulse dose alone indicating a benefit using the immunotherapy. This further suggests that large ablative pulses may stimulate an immune response and that subsequent pulses of radiation given in quick succession, rather than with a more prolonged split course, can negate the positive immune responses.

Embodiments of the present disclosure relate to methods of adaptive treatment of a tumor in a subject that include ablative defined as disrupting both tumor cell proliferation and target cell function or near-ablative doses of radiation administered on a split-course basis (i.e. at least one week apart). In some embodiments, the pulse doses may be part of a SABR treatment, employing sophisticated targeting, motion control, image guidance and compact dosimetry primarily treating the gross tumor with minimal margin. In some embodiments, the timeframe between doses may be optimized and adapted by use of personalized feedback, allowing for radiotherapy to be tailored to specific patients, thereby avoiding over- and under-treatment. For example, a tumor that shrinks very quickly may benefit from a longer rest/observation period between treatments to facilitate better downstream adaptation without tumor control penalty. This adaptation may also facilitate a considerably improved synergy between radiotherapy and systemic therapies, such as immunotherapy or even a synergy with surgery. For example, when using radiation therapy pre-operatively, a potent pulse or pulses might allow optimal tumor shrinkage away from critical structures that might otherwise be damaged by surgery. Furthermore, longer periods of time between doses may substantially increase the quality of life of patients by avoiding the burden of days on end with consecutive treatments. By analyzing a patient's data relating to tumor response and toxicity for changes, a more personalized and adaptive treatment plan can be generated for a specific patient.

Figure 5:
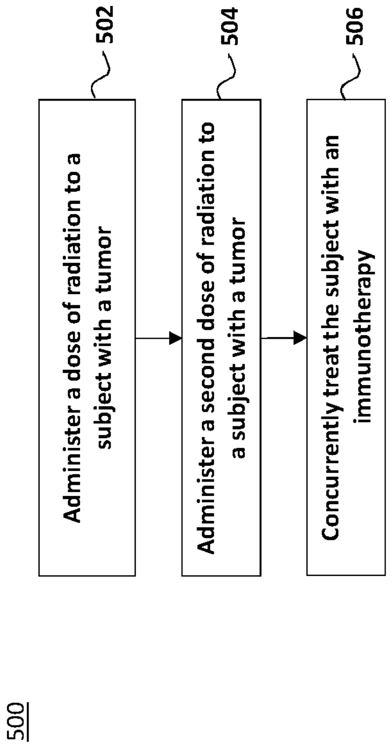
FIG. 5 is a flowchart showing a method of adaptive treatment of a subject with a tumor, according to some embodiments of the present disclosure.

FIG. 5 is a flowchart showing a method 500 of adaptive treatment of a subject with a tumor, according to some embodiments of the present disclosure. Patients eligible for this adaptive treatment include those with more limited primary tumors (e.g., early stages) as well as patients with more advanced disease (e.g., those with regional or metastatic disease). At block 502, a first test dose of radiation, called the first pulse, may be administered to a tumor within a subject. The tumor may be either benign or malignant. In all embodiments, the dose may be substantial enough to initiate changes in the tumor, tumor environment, or within the patient better facilitating adaptation and personalization. To this end, the pulse dose may be at least 6-8 Gy, possibly more. In some embodiments, the dose may be ablative, defined as disrupting both proliferative capacity and cellular function, and used conventionally as standalone therapy for both primary cancers and metastases. Such doses range from 15-50 Gy per treatment. Often, ablative dose range causes widespread tumor death. For example, the dose may be a dose similar to or the same as a dose that would be applied in stereotactic ablative radiotherapy (SABR). Doses currently used for the first or only fraction in existing SABR treatments for solid tumors range from 8-50 Gy. For example, the dose may be applied with high accuracy and precision and intentionally limited to the gross tumor/cancer, which may mitigate the effects of radiation to normal tissue surrounding the tumor. At block 504, a second pulse dose of radiation may be administered to the subject. In some embodiments, the period of time (i.e. rest/observation period) between the first and second doses may be at least 6-7 days or more. For example, a first dose of 10 Gy may be administered and, 10 days later, a second dose of 10 Gy may be administered. In some embodiments, the rest/observation period may be 10 days, 20 days, 30 days, or even months long. In some embodiments, the second dose may also be ablative and similar to or the same as a dose that would be applied in stereotactic ablative radiotherapy. The second dose may have the same or different potency targeting a larger or smaller target field as the first dose. In some embodiments, the second and subsequent pulse dose levels may be modified or adapted based on information obtained during the rest/observation period or periods.

For example, the adaptation impacting the second pulse dose level may be so simple as reducing the dose if the tumor shrinks dramatically after the first pulse. Conversely, the second pulse dose may be larger than the first if the tumor failed to respond or even grew after the first pulse. When tumors respond after the first or any previous pulse, the next planned pulse may treat the smaller volume as an adaptation. Another example may be that the previous pulse caused new hypoxia based on imaging that constitutes focal radioresistance. In response, an additional dose may be "painted" using dosimetric modulation to these hypoxic areas when planning the upcoming pulse. In response, a hypoxic cell sensitizing drug may be given in addition to the next radiation pulse.

Another example might be that sampling of circulating tumor cells or repeat biopsy or other laboratory or imaging changes indicate that the targeted tumor(s) might benefit from the addition of a specific class of drugs, targeted therapy, or immunotherapy. In this circumstance, the subsequent pulse might be delivered along with this drug or combination treatment in a fashion that is known to optimize the com. Another example may be that the tumor response indicates that radiation alone will never eliminate the patient's particular tumor. In this circumstance, the patient may be referred for surgery or drug therapy without radiation. The process of providing pulses of dose in this fashion may be repeated either until the cancer is eliminated (cured), the treatment causes unacceptable toxicity, or until tumor progression occurs despite all adaptive options/opportunities being exhausted.

In some embodiments, prior to performing block 504 and administering the second dose of radiation to the subject with a tumor, a level of radiation or potency, duration of the rest/observation period, and target field for the second dose may be determined using a machine learning model. For example, artificial intelligence and machine learning may be utilized to personalize and adapt the treatment therapy to a specific patient based on their response to an initial dose of radiation. In some embodiments, the machine learning model may employ reinforcement learning algorithms. The patient's response to the initial dose may encompass a wide variety of factors including, but not limited to, symptoms, exams, imaging, tumor response, blood tests, bodily fluid analysis, biopsies, histology, grade, stage, genomics, sequencing, gene expression, performance, patient tolerance, attitude, social circumstances, or any other personal test. Because the rest/observation period between doses is relatively long, meaning not on back to back days and ideally more than seven days, there is ample time for the patient's body and the tumor to adapt. The AI or machine learning model may be trained to analyze these factors and changes and determine characteristics for a subsequent dose. For example, if a tumor is determined to have characteristics that suggest a high risk for rapid growth, the rest period between doses may be shorter than when tumor shrinkage has been detected. Furthermore, extra time between pulses may allow immune cascades to run their designed course throughout the body, making subsequent pulses more effective. In some embodiments, the machine learning model may also be trained to determine whether or not concurrent therapies, such as immunotherapy, should be continued, discontinued, or changed.

In some embodiments, the AI or machine learning model may be trained to analyze at least one of radiomic and biologic features. Biologic features may include target tissue vascularity, normal tissue vascularity, target tissue oxygenation status, normal tissue oxygenation status, target tissue cytokine profile, normal tissue cytokine profile, target tissue gene expression, normal tissue gene expression, target tissue receptor expression, normal tissue receptor expression, target tissue white blood cell infiltration, normal tissue white blood cell infiltration, tumor markers, tumor burden, systemic immune status, changes in subject health, and changes in patient weight.

In some embodiments, radiomic features may include features extracted from, or images from, anatomical imaging characteristics (e.g., tumor response, tumor infiltration, edge features, density features, shape features, etc.), functional imaging characteristics (e.g., blood flow, enhancement, etc.), and metabolic imaging characteristics (e.g., glucose uptake, proliferation, hypoxia, etc.).

The machine learning model may be trained on a clinical trial in a subset of patients. Baseline and follow-up features may be mined and may constitute a training set for the model. Separate and typically larger datasets typically validate the model. Ongoing treated patient features may serve to improve the accuracy of the reinforcement learning algorithms utilized by the machine learning model.

At block 506, the subject may be concurrently treated with an immunotherapy. In some embodiments, an immune stimulating drug, or immune stimulant, may be administered with a pulse dose of radiation. In some embodiments, this may be administered with each pulse dose of radiation, and not just the initial dose. In some embodiments, the immune stimulant may include a checkpoint inhibitor. In some embodiments the immune stimulant may include cytokines such as IL-2. In some embodiments, the immune stimulant may include tumor derived immune stimulants. In some embodiments the immune stimulant may include drugs impacting the cGAS STING pathway that is felt to play a central role in improved DNA sensing resulting from radiation damage to tumor cells and the tumor microenvironment. The immune stimulating drugs may be given in appropriate dosage typically in close proximity to the radiation pulses such that the two treatments might act in concert for maximal effect. In some embodiments, the use of multiple pulse doses, either with constant dose/volume pulses or with variable dose and variable volume pulses related to adaptation, may act as an immunizing "booster shot" akin to the way common viral immunizations are given to patients with initial shots followed by booster shots aimed at causing a more profound and lasting adaptive immune response. In some embodiments, these booster shot-like pulses may be given with immune stimulating drugs as just described.

Figure 6:
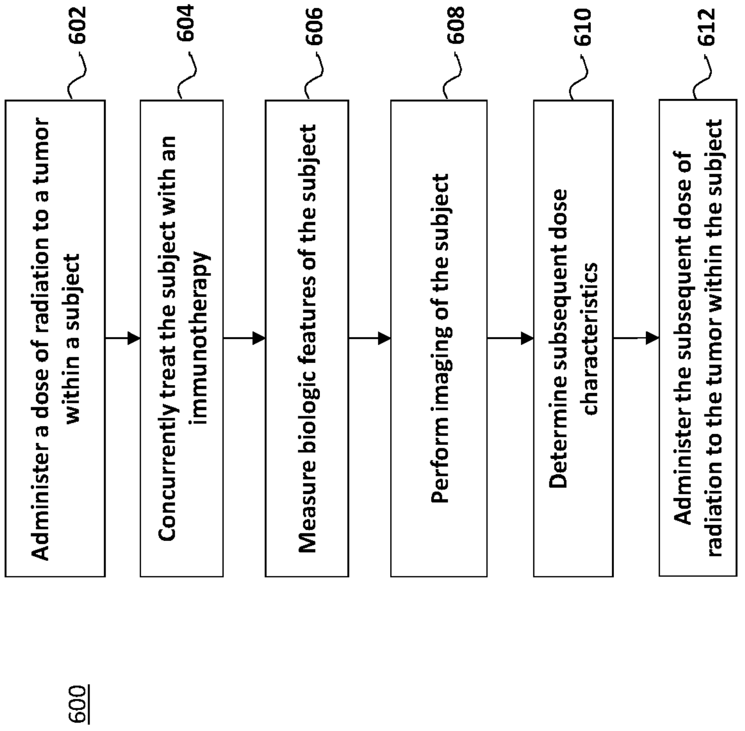
FIG. 6 is a flowchart showing another method of adaptive treatment of a subject with a tumor, according to some embodiments of the present disclosure.

FIG. 6 is a flowchart showing method 600 of adaptive treatment of a subject with a tumor, according to some embodiments of the present disclosure. Patients eligible for this adaptive treatment include those with more limited primary tumors (e.g., early stages) as well as patients with more advanced disease (e.g., those with regional or metastatic disease). In this adaptive treatment, an approach using immunotherapy or immune stimulating drugs may be appropriate from the onset based on patient characteristics. At block 602, a dose of radiation may be administered to a tumor within a subject. In some embodiments, the tumor may be benign or malignant. In some embodiments, the dose may be ablative and may be similar to or the same as, or part of, a radiotherapy comprising stereotactic ablative radiotherapy (SABR). At block 604, the subject may be treated concurrently with an immunotherapy. In some embodiments, this may include administering an immune stimulant, or immune-stimulating drug, to the subject with at least one pulse dose of radiation. In some embodiments, the immune stimulant may be a checkpoint inhibitor, an immune stimulating cytokine, a tumor derived immune stimulant, an agent associated with the cGAS STING pathway, or other immune stimulating drugs.

At block 606, biologic features of the subject may be measured during the rest/observation period. Measurements may be taken at any point after the pulse dose, however, many features may require waiting many days, weeks or even months to detect. In some embodiments, the biologic features may be measured as a method of detecting the body's and tumor's response to the first pulse dose or any previous pulse dose of radiation.

At block 608, imaging of the subject may be performed. Imaging may include anatomical imaging, functional imaging, and metabolic imaging. In some embodiments, radiomics may be used to extract features from the imaging results. At block 610, characteristics of a subsequent dose may be determined. In some embodiments, this may be determined using an artificial intelligence or machine learning model. The model may be the same as or similar to the model described in relation to block 504 of FIG. 5. The model may be trained to analyze at least one of biologic and imaging characteristics of the patient. In some embodiments, the model may determine a level of radiation or potency, duration of the rest period, and target field for the subsequent dose. At block 612, the subsequent dose may be administered to the tumor within the subject according to the determined characteristics of block 610.

Note that both methods 500 and 600, as described in relation to FIGS. 5 and 6, are radiation-type agnostic. Any ionizing radiation including, but not limited to, photons, electrons, protons, heavier charged particles, neutrons, etc. may be employed. Furthermore, any mode of delivery of the ionizing radiation may be utilized, including, but not limited to static beam, scanning, rotational, 3-D, intensity-modulated, and at any dose rate including FLASH radiotherapy at ultra-high dose rates (>70-100 Gy/sec).

In order to test various methods as described herein, pre-clinical trials were performed on mice. Cancer cell lines (e.g., MC38 and LLC) were cultured in 5% CO2 and maintained in vitro in Dulbecco's modified Eagle's medium supplemented with 10% heat-inactivated fetal bovine serum, 100 U/ml penicillin, and 100 μg/ml streptomycin. MC38 can include a colon cancer model in the C57BL/6 background known to have infiltration of CD8+T cells in the untreated tumor microenvironment (ref) and responds to anti-PDL1 monotherapy and can be referred to as a "hot" tumor environment herein. LLC can be referred to as a "cold" tumor environment and is a syngeneic tumor model in the C57BL/6 background known to be non-immunogenic (e.g., cold) and does not respond to anti-PDL1 monotherapy. All cell lines were routinely tested for mycoplasma contamination and were confirmed negative prior to the trial. In some embodiments, Anti-CD8 clone 53-6.7 can be used for LLC experiments and anti-CD8 clone 53-5.8 for MC38. Additionally, anti-PD-L1 (10F.9G2, referred to as a-PDL herein) and an isotype control for a-PDL can be clone LTF-2. In some embodiments, for MC38 trials, radiation pulses of 8 Gy can be given and, for LLC trials, radiation pulses of 10-15 Gy can be given.

For trials, tumor cells can be injected subcutaneously on the right leg of mice. Mice can be randomized to treatment groups when tumors reached 150-200 $mm^3$ for LLC and 100-150 $mm^3$ for MC38. Tumors were treated with anti-PD-L1 or not, then tumor volumes were measured by the length (a), width (b) and height (h) and calculated as tumor volume=abh/2. For the survival curve, if each of length, width or height of tumor is larger than 2 cm, the tumor volume is larger than 1500 $mm^3$, or the mice had a significant ulceration in the tumor, the mice were considered dead. For CD8 T cell depletion experiments, 200 μg anti-CD8 was given intraperitoneally on the same day of first antibody treatment, and every four days for a total of three weeks. For the experiments in MC38, 25 μg anti-PDL1 or 25 μg anti-PDL1 isotype was administered intraperitoneally to mice every two days for a total of four times starting one day before radiation. For the experiments in LLC, 200 μg anti-PDL1 or 200 μg anti-PDL1 isotype was administered intraperitoneally to mice every two days for a total of four times starting 2 days before radiation.

Figure 7A:
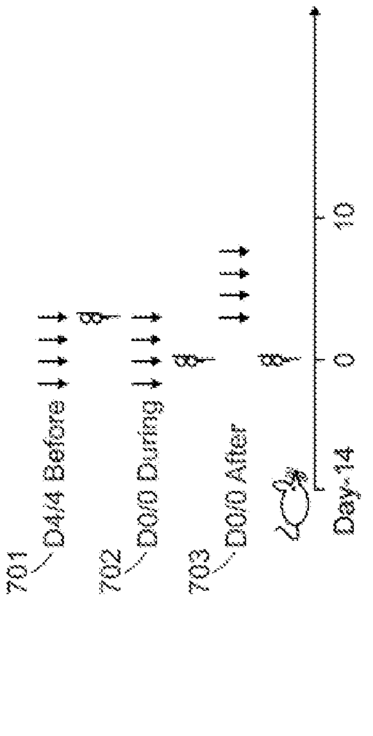
FIGS. 7A-7D show a sequence of immunotherapy and radiation therapy within radio-immunotherapy pulses and impacts on tumor growth, according to some embodiments of the present disclosure.

FIGS. 7A-7D show a sequence of immunotherapy and radiation therapy within radio-immunotherapy pulses and impacts on tumor growth, according to some embodiments of the present disclosure. The studies and results, as shown in FIGS. 7A-7D, describe various efforts to study tumor growth based on the timing between pulses of radiation and doses of immunotherapy on an immunogenic tumor (e.g., MC38). FIG. 7A shows three treatment schedules that were studied: treatment schedule 701 involves administering a radiation dose after immunotherapy (e.g., four doses of anti-PDL1 followed by a pulse of sixteen Gy). Treatment schedule 702 involves administering a radiation dose during immunotherapy (e.g., four doses of anti-PDL1 with a pulse of sixteen Gy at the second dose). Treatment schedule 703 involves administering a radiation dose before immunotherapy (e.g., a pulse of sixteen Gy followed by four doses of anti-PDL1). The doses of anti-PDL1 are administered on consecutive days.

Figure 7B:
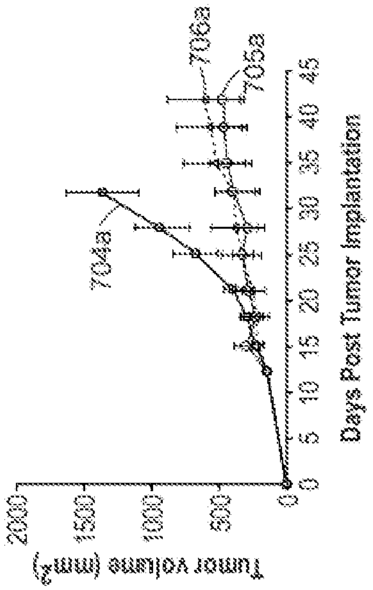

FIG. 7B is a plot of tumor volume (y-axis in cubic millimeters) over time (x-axis in days) for treatment schedule 701. Line 704*a* is a plot of tumor growth when only using an isotype. Line 705*a* is a plot of tumor growth when only using radiation (e.g., single pulse of sixteen Gy). Line 706*a* is a plot of tumor growth when using radiation and anti-PDL1 as described in treatment schedule 701. Here, there was little additive effect of anti-PDL1 therapy combined with radiation.

Figure 7C:
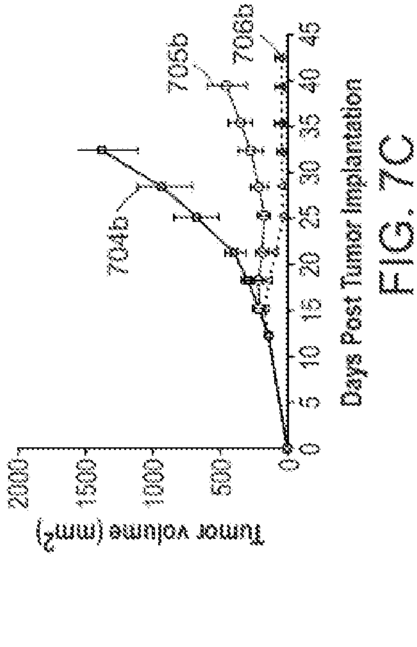

FIG. 7C is a plot of tumor volume (y-axis in cubic millimeters) over time (x-axis in days) for treatment schedule 702. Line 704*b* is a plot of tumor growth when only using an isotype. Line 705*b* is a plot of tumor growth when only using radiation (e.g., single pulse of sixteen Gy). Line 706*b* is a plot of tumor growth when using radiation and anti-PDL1 as described in treatment schedule 702. Here, there is reduced tumor growth for treatment according to treatment schedule 702.

Figure 7D:
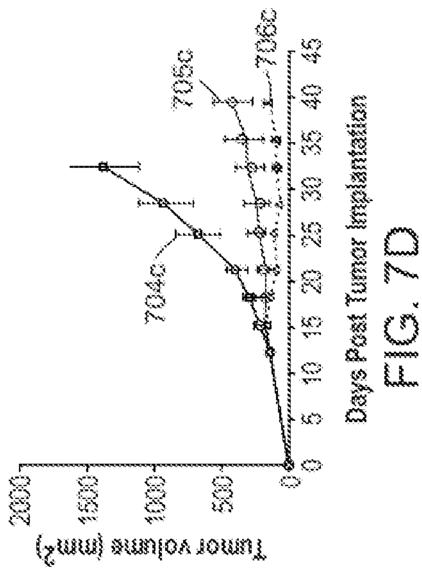

FIG. 7D a plot of tumor volume (y-axis in cubic millimeters) over time (x-axis in days) for treatment schedule 703. Line 704*c* is a plot of tumor growth when only using an isotype. Line 705*c* is a plot of tumor growth when only using radiation (e.g., single pulse of sixteen Gy). Line 706*c* is a plot of tumor growth when using radiation and anti-PDL1 as described in treatment schedule 703. Here, there is reduced tumor growth for treatment according to treatment schedule 703.

Figure 8A:
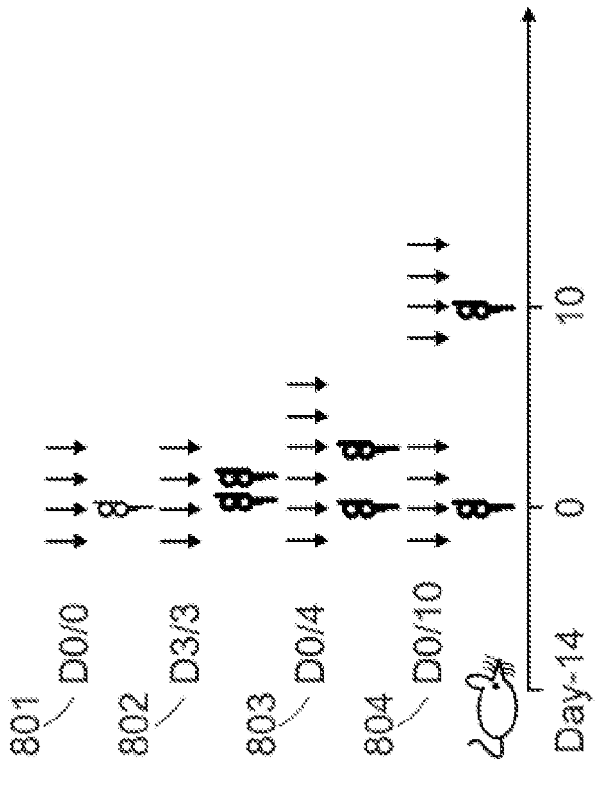
FIGS. 8A-8E show timing of radio-immunotherapy pulses and effects on tumor growth in a hot tumor microenvironment, according to some embodiments of the present disclosure.

FIGS. 8A-8E show timing of radio-immunotherapy pulses and effects on tumor growth in a hot tumor microenvironment, according to some embodiments of the present disclosure. FIG. 8A shows various treatment schedules based on applying multiple pulses of radiation, as compared to a single pulse of radiation in FIGS. 7A-7D. As described in relation to FIGS. 8A-8E, a "fraction" includes four consecutive doses of anti-PDL1, with a radiation pulse of sixteen Gy at the same time (e.g., the same day) as the second dose, similar to as described in FIGS. 7A and 7C. Treatment schedule 801 involves two fractions, timed such that the two radiation pulses occur on the same day. Treatment schedule 802 involves two fractions, timed such that the two radiation pulses occur one day apart. Treatment schedule 803 involves two fractions, timed such that the two radiation pulses occur four days apart. Treatment schedule 804 involves two fractions, timed such that the two radiation pulses occur ten days apart. In some embodiments, ten days may reflect the timing of when newly primed T cells would enter a tumor microenvironment from a draining lymph node.

Figure 8B:
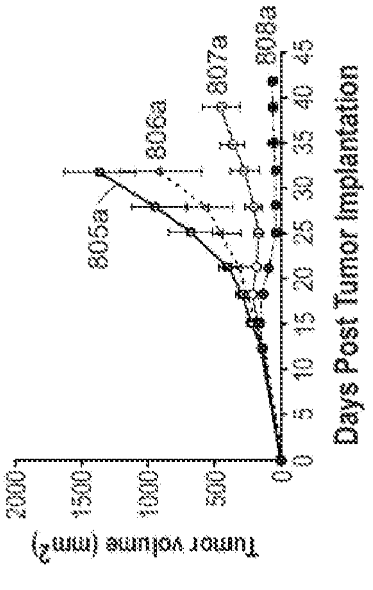

FIG. 8B is a plot of tumor volume (y-axis in cubic millimeters) over time (x-axis in days) for treatment schedule 801. Line 805*a* is a plot of tumor growth when only using an isotype. Line 806*a* is a plot of tumor growth when only using anti-PDL1 as a treatment. Line 807*a* is a plot of tumor growth when only using radiation (e.g., single pulse of sixteen Gy). Line 808*a* is a plot of tumor growth when using radiation and anti-PDL1 as described in treatment schedule 801.

Figure 8C:
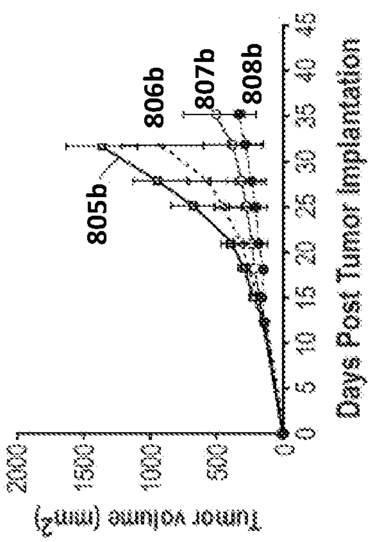

FIG. 8C is a plot of tumor volume (y-axis in cubic millimeters) over time (x-axis in days) for treatment schedule 802. Line 805*b* is a plot of tumor growth when only using an isotype. Line 806*b* is a plot of tumor growth when only using anti-PDL1 as a treatment. Line 807*b* is a plot of tumor growth when only using radiation (e.g., single pulse of sixteen Gy). Line 808*b* is a plot of tumor growth when using radiation and anti-PDL1 as described in treatment schedule 802.

Figure 8D:
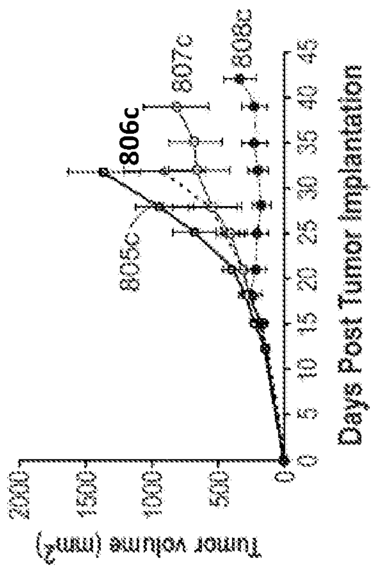

FIG. 8D is a plot of tumor volume (y-axis in cubic millimeters) over time (x-axis in days) for treatment schedule 803. Line 805*c* is a plot of tumor growth when only using an isotype. Line 806*c* is a plot of tumor growth when only using anti-PDL1 as a treatment. Line 807*c* is a plot of tumor growth when only using radiation (e.g., single pulse of sixteen Gy). Line 808*c* is a plot of tumor growth when using radiation and anti-PDL1 as described in treatment schedule 803.

Figure 8E:
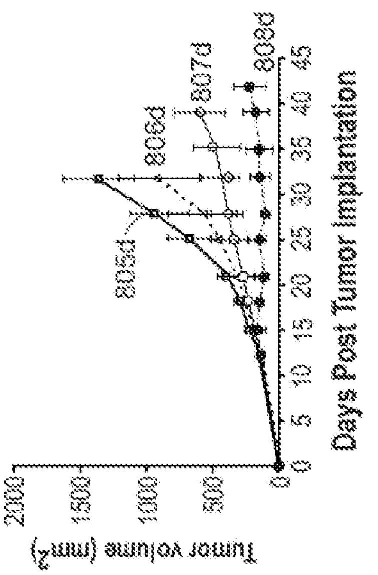

FIG. 8E is a plot of tumor volume (y-axis in cubic millimeters) over time (x-axis in days) for treatment schedule 804. Line 805*d* is a plot of tumor growth when only using an isotype. Line 806*d* is a plot of tumor growth when only using anti-PDL1 as a treatment. Line 807*d* is a plot of tumor growth when only using radiation (e.g., pulses of sixteen Gy). Line 808*d* is a plot of tumor growth when using radiation and anti-PDL1 as described in treatment schedule 804. Based on the results of FIGS. 8A-8E, tumor control (e.g., tumor growth was more limited) saw more improvements when using treatments 801, 803, and 804 than it did for treatment 802.

Figure 9A:
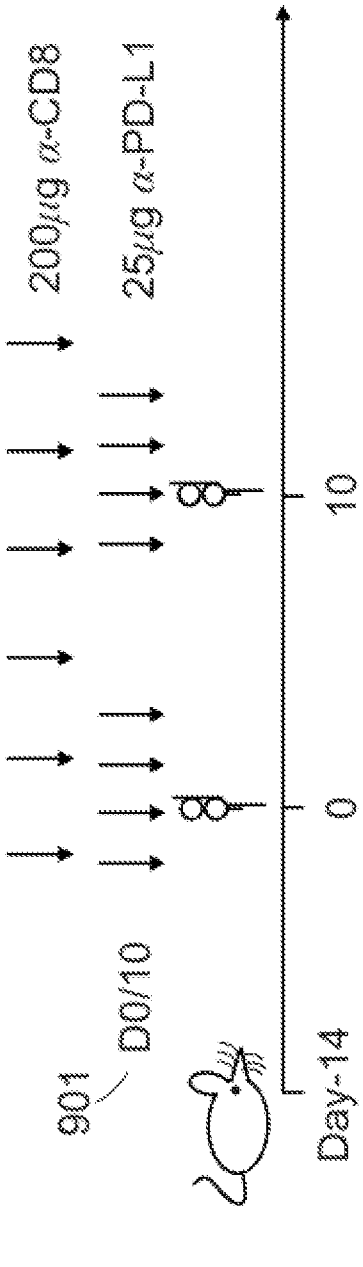
FIGS. 9A-9C shows a response to pulsed radio-immunotherapy and dependences on CD8+ T cells and immunological memory, according to some embodiments of the present disclosure.
Figure 9B:
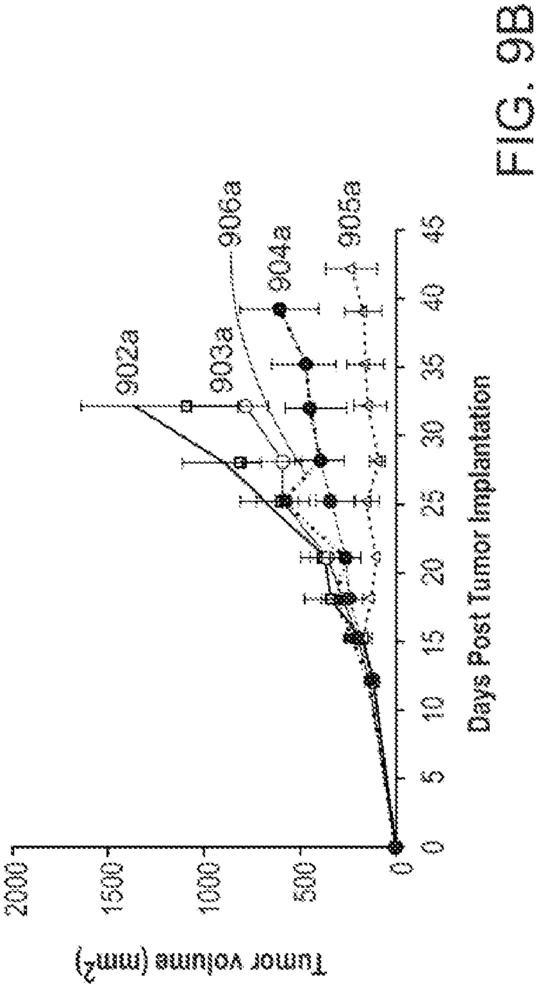
Figure 9C:
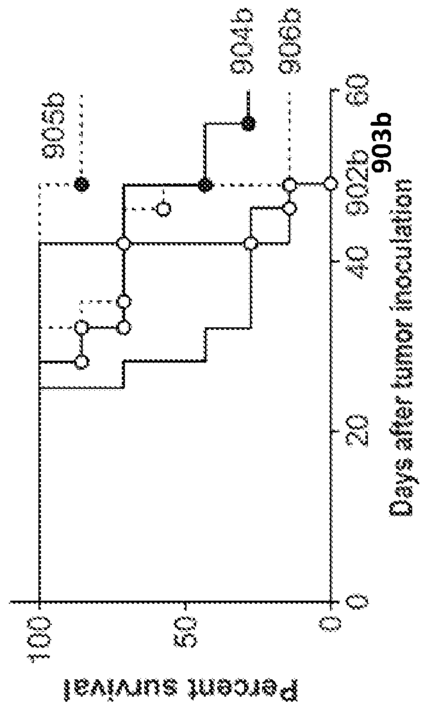

FIGS. 9A-9C shows a response to pulsed radio-immunotherapy and dependences on CD8+ T cells and immunological memory, according to some embodiments of the present disclosure. FIG. 9A depicts a treatment schedule 901 that is used and varied to study whether the synergy between pulsed radio-immunotherapy was still immune dependent. Treatment schedule 901 involves a schedule similar to as described in treatment schedule 804, including two fractions, such that the radiation pulse of each fraction is ten days apart. The immunotherapy drug is varied to study immune-related effects. FIG. 9B is a plot of tumor volume (y-axis in cubic millimeters) over time (x-axis in days). Line 902*a* is a plot of tumor growth when only using an isotype. Line 903*a* is a plot of tumor growth when using radiation, an isotype instead of anti-PDL1, and anti-CD8 (e.g., 200 μg of an anti-CD8 depleting antibody). Line 904*a* is a plot of tumor growth when using radiation and isotype as described in treatment schedule 901. Line 905*a* is a plot of tumor growth when using radiation and anti-PDL1 as described in treatment schedule 901. Line 906*a* is a plot of tumor growth when using radiation, anti-PDL1, and anti-CD8.

FIG. 9C involves a survival plot of mice, showing percent survival (y-axis) as a function of time (x-axis, in days). Lines 902*b*-906*b* correspond, respectively, to the treatments described in lines 902*a*-906*a*. The results of FIG. 9B-9C suggest radiation and anti-PDL1 (905*a*-*b*) offer the most control of the tumor and that the introduction of the CD8 depleting antibody did not have large effects.

Figure 10A:
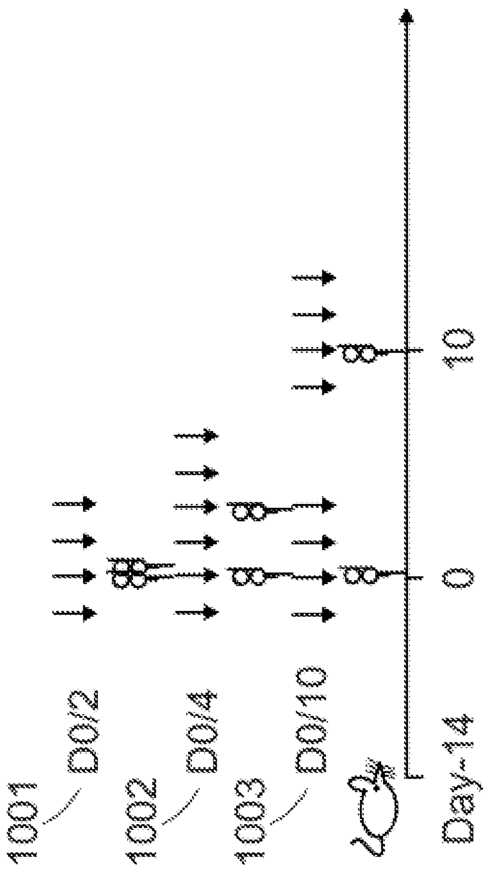
FIGS. 10A-10E show synergistic anti-tumor effects that depend on radiation dose and schedule from radio-immunotherapy pulses in cold immune-resistant tumors, according to some embodiments of the present disclosure.

FIGS. 10A-10E show synergistic anti-tumor effects that depend on radiation dose and schedule from radio-immunotherapy pulses in cold immune-resistant tumors, according to some embodiments of the present disclosure. For the studies as described in FIGS. 10A-10E, a "cold" tumor, or an LLC tumor is studied in mice. In some embodiments, this suggests that an LLC tumor does not typically respond to anti-PDL1 therapy. FIG. 10A illustrates three treatments: treatment involving two fractions. As described in relation to FIGS. 10A-10E and similar to FIGS. 8A-8E, a "fraction" includes four consecutive doses of anti-PDL1, with a radiation pulse of sixteen Gy at the same time (e.g., the same day) as the second dose, similar to as described in FIGS. 7A and 7C. Treatment schedule 1001 involves two fractions, timed such that the two radiation pulses occur one day apart. Treatment schedule 1002 involves two fractions, timed such that the two radiation pulses occur four days apart. Treatment schedule 1003 involves two fractions, timed such that the two radiation pulses occur ten days apart.

Figure 10B:
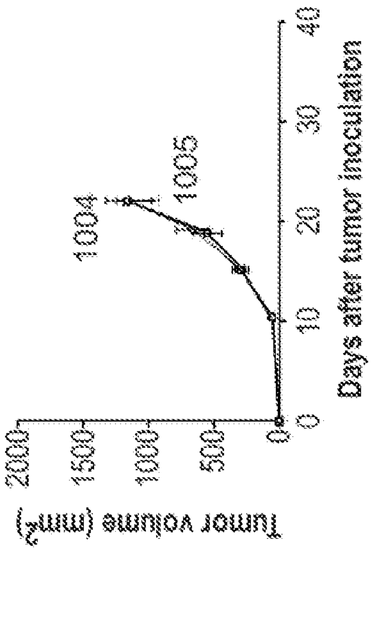
Figure 10C:
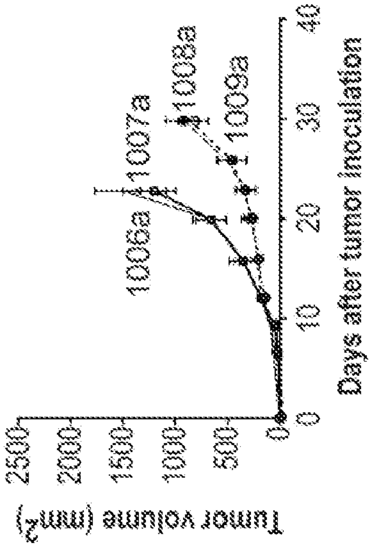

FIG. 10B shows a plot of tumor volume (y-axis in cubic millimeters) over time (x-axis in days) for a treatment involving just an isotype (line 1004) and just anti-PDL1 (line 1005). As expected, considering the LLC tumor is "cold," there is little tumor control and substantial growth. FIG. 10C shows a plot of tumor volume (y-axis in cubic millimeters) over time (x-axis in days) for treatment schedule 1001. Line 1006*a* is a plot of tumor growth when only using an isotype. Line 1007*a* is a plot of tumor growth when only using anti-PDL1 as a treatment. Line 1008*a* is a plot of tumor growth when using radiation and isotype according to treatment schedule 1001. Line 1009*a* is a plot of tumor growth when using radiation and anti-PDL1 as described in treatment schedule 1001 (e.g., radiation pulses one day apart).

Figure 10D:
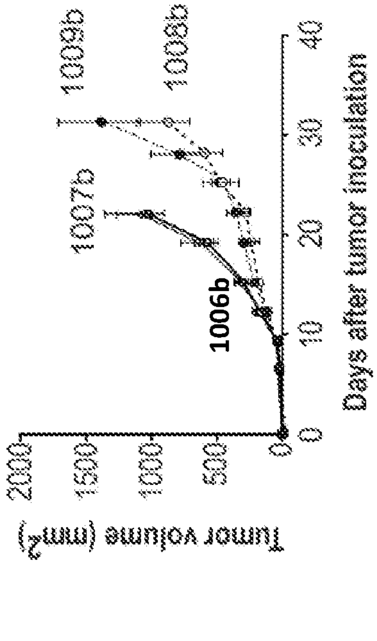

FIG. 10D shows a plot of tumor volume (y-axis in cubic millimeters) over time (x-axis in days) for treatment schedule 1002. Line 1006*b* is a plot of tumor growth when only using an isotype. Line 1007*b* is a plot of tumor growth when only using anti-PDL1 as a treatment. Line 1008*b* is a plot of tumor growth when using radiation and isotype according to treatment schedule 1001. Line 1009*b* is a plot of tumor growth when using radiation and anti-PDL1 as described in treatment schedule 1002 (e.g., radiation pulses four days apart).

Figure 10E:
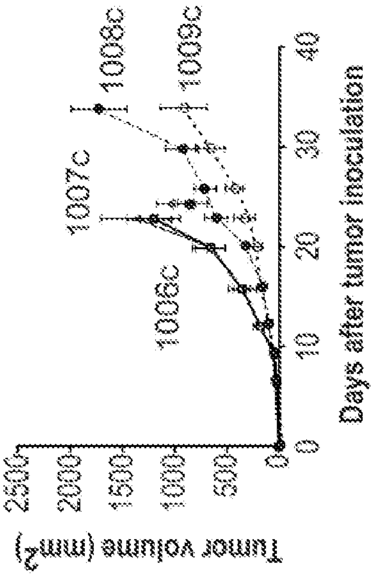

FIG. 10E shows a plot of tumor volume (y-axis in cubic millimeters) over time (x-axis in days) for treatment schedule 1003. Line 1006*c* is a plot of tumor growth when only using an isotype. Line 1007*c* is a plot of tumor growth when only using anti-PDL1 as a treatment. Line 1008*c* is a plot of tumor growth when using radiation and isotype according to treatment schedule 1001. Line 1009*c* is a plot of tumor growth when using radiation and anti-PDL1 as described in treatment schedule 1003 (e.g., radiation pulses ten days apart). Treatment schedules 1001 and 1002 do not have noticeable impacts on tumor control. However, treatment schedule 1003 suggests a synergistic anti-tumor effect.

Figure 11A:
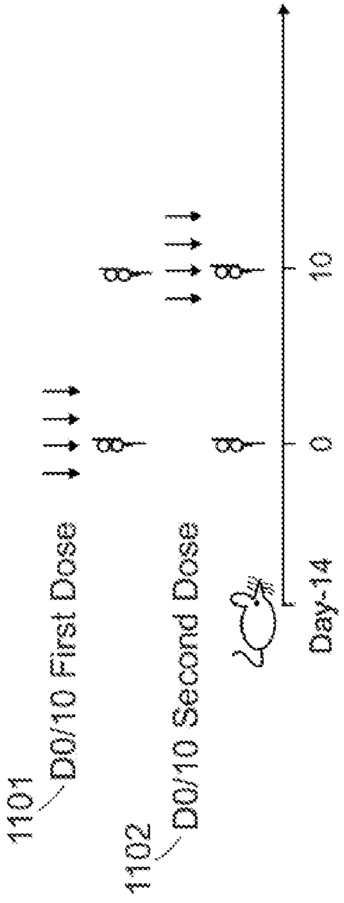
FIGS. 11A-11D shows a response to pulsed radio-immunotherapy and dependences on CD8+ T cells and immunological memory, according to some embodiments of the present disclosure.

FIGS. 11A-11D shows a response to pulsed radio-immunotherapy and dependences on CD8+ T cells and immunological memory, according to some embodiments of the present disclosure. FIG. 11A depicts various treatments that are used to study which dose of anti-PDL1 has the most effectiveness. In treatment 1101, mice are given two pulses of radiation, with the immunotherapy (e.g., the anti-PDL1 doses) only given in coordination with the first pulse. In treatment 1102, mice are given two pulses of radiation, with the immunotherapy only given in coordination with the second pulse. In both treatments, the radiation pulses are ten days apart.

Figure 11B:
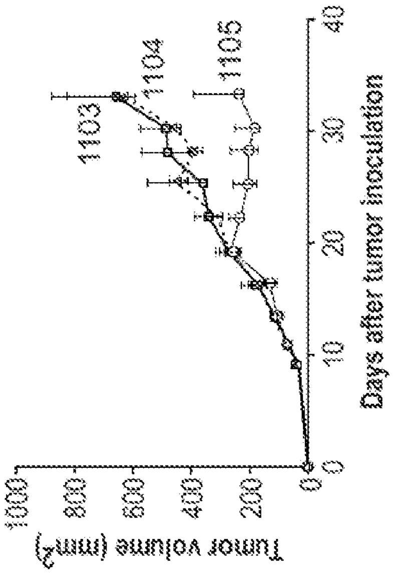

FIG. 11B shows a plot of tumor volume (y-axis in cubic millimeters) over time (x-axis in days). Line 1103 is a plot of tumor growth when using radiation in combination with an isotype. Line 1104 is a plot of tumor growth when using radiation and anti-PDL1 as described in treatment 1101.

Line 1105 is a plot of tumor growth when using radiation and anti-PDL1 as described in treatment 1102. The tumor control in treatment 1102 is better than with treatment 1102.

Line 1006*a* is a plot of tumor growth when only using an isotype. Line 1007*a* is a plot of tumor growth when only using anti-PDL1 as a treatment. Line 1008*a* is a plot of tumor growth when using radiation and isotype according to treatment schedule 1001. Line 1009*a* is a plot of tumor growth when using radiation and anti-PDL1 as described in treatment schedule 1001 (e.g., radiation pulses one day apart).

Figure 11C:
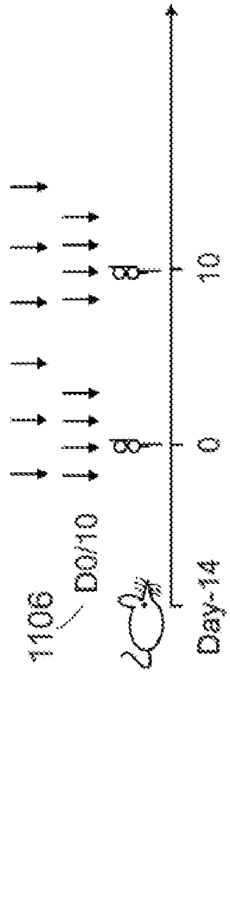
Figure 11D:
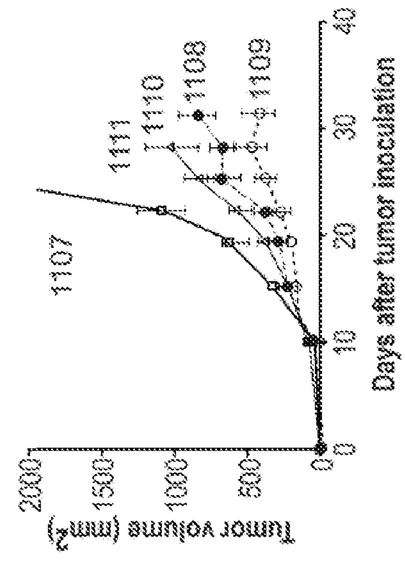

FIG. 11C shows a treatment schedule 1106. Treatment schedule 1106 involves variations similar to those described in FIGS. 9A-9C. FIG. 11C depicts a treatment schedule 1106 that is used and varied to study whether the synergy between pulsed radio-immunotherapy was still immune dependent. Treatment schedule 1006 involves a schedule similar to as described in treatment schedule 804, including two fractions, such that the radiation pulse of each fraction is ten days apart. The immunotherapy drug is varied to study immune-related effects (e.g., between anti-PDL1 and anti-CD8). FIG. 11D shows a plot of tumor volume (y-axis in cubic millimeters) over time (x-axis in days). Line 1107 is a plot of tumor volume over time for a treatment involving only an isotype. Line 1108 is a plot of tumor growth when using radiation and an isotype as described in treatment schedule 1106. Line 1109 is a plot of tumor growth over time when using radiation and anti-PDL1. Line 1110 is a plot of tumor growth when using radiation, an isotype instead of anti-PDL1, and anti-CD8 (e.g., 200 μg of an anti-CD8 depleting antibody). Line 1111 is a plot of tumor growth when using radiation, anti-PDL1, and anti-CD8. Similar to as shown in FIGS. 9A-9C, synergy is lost in treated groups receiving anti-CD8 depleting antibodies.

The results as described in FIGS. 7A-11E suggest that SAbR ranges of radiotherapy in combination with anti-PDL1 (PDL1 antibody inhibition) can improve tumor control in both hot and cold tumors and potentially produces an abscopal effect, which involves adaptive immunity. This is further shown below in FIGS. 12A-12B.

Figure 12A:
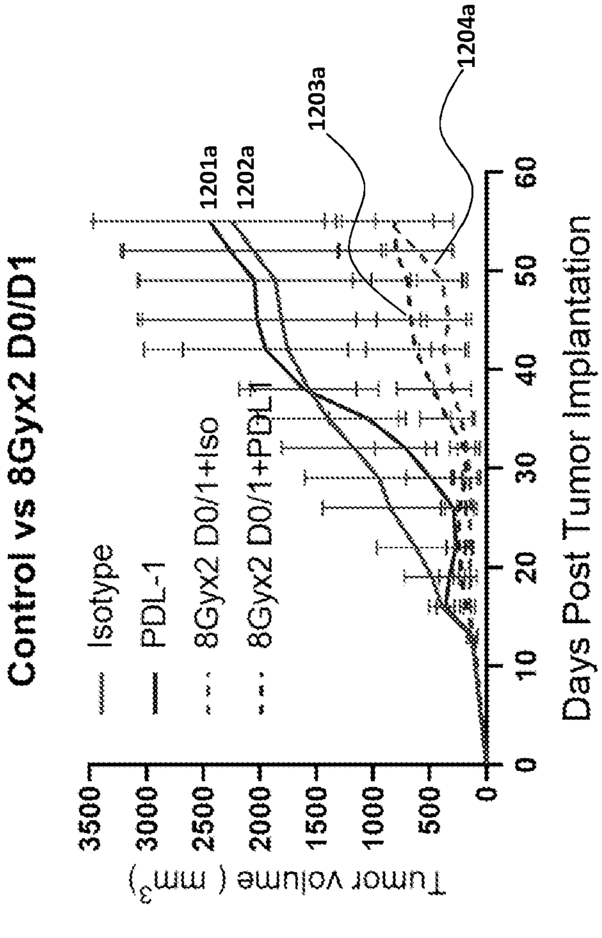
FIGS. 12A-12B show plots of tumor growth as a function of time, according to some embodiments of the present disclosure.
Figure 12B:
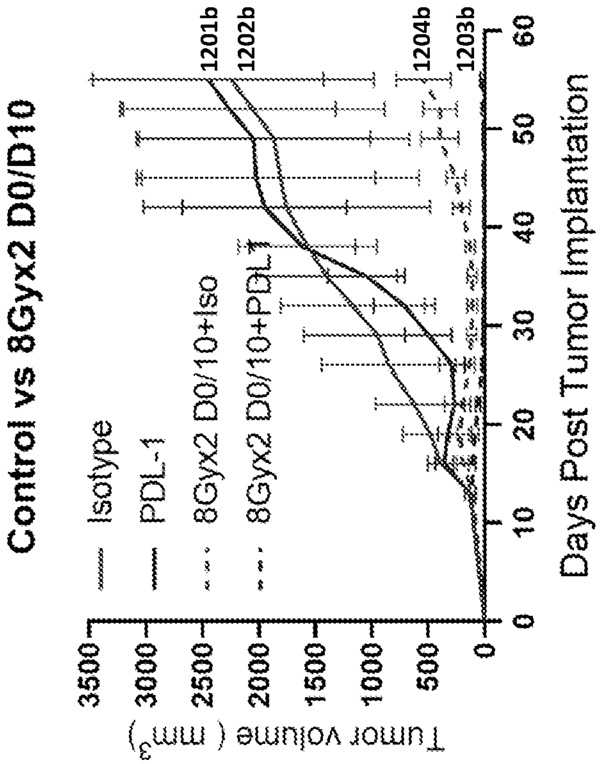

FIGS. 12A-12B show plots of tumor growth as a function of time, according to some embodiments of the present disclosure. Both FIGS. 12A-12B involve treatment of mice with MC38 tumors implanted. FIG. 12A shows a plot of tumor volume (y-axis in cubic millimeters) over time (x-axis in days) for radiation pulses separates by one day. Line 1201*a* shows tumor growth over time when solely treating mice with anti-PDL1. Line 1202*a* shows tumor growth over time when solely using an isotype on mice. Line 1203*a* shows tumor growth over time when using radiation in combination with anti-PDL1. Line 1204*a* shows tumor growth over time when using radiation in combination with an isotype. Lines 1201*a*-1204*a* all exhibit tumor control penalties and do not inhibit tumor growth.

FIG. 12B also shows a plot of tumor volume (y-axis in cubic millimeters) over time (x-axis in days) for radiation pulses separates by ten days. Line 1201*b* shows tumor growth over time when solely treating mice with anti-PDL1. Line 1202*b* shows tumor growth over time when solely using an isotype on mice. Line 1203*b* shows tumor growth over time when using radiation in combination with anti-PDL1. Line 1204*b* shows tumor growth over time when using radiation in combination with an isotype. Lines 1201*b*, 1202*b*, and 1204*b* each exhibit tumor control penalties and do not inhibit tumor growth. Line 1203*b*, however, shows significant tumor control and suggests potentially cured or curable mice.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing illustrative embodiments, it is understood that the present disclosure has been made only by way of example, and that numerous changes in the details of implementation of the disclosed subject matter may be made without departing from the spirit and scope of the disclosed subject matter.

The invention claimed is:

1. A method of adaptive treatment of a subject with a tumor comprising:

administering a first pulse dose of radiation to the tumor within the subject;

in response to administering the first pulse dose, determining, using a machine learning model, at least a duration of an observation period;

administering a second pulse dose of radiation to the tumor, wherein the second pulse dose is administered after the observation period, the observation period having the duration of at least 7 days; and concurrently treating the subject with an immunotherapy.

2. The method of claim 1, wherein the first and second pulse doses of radiation are ablative.

3. The method of claim 2, wherein the first and second pulse doses are part of a radiotherapy, the radiotherapy comprising stereotactic ablative radiotherapy (SABR).

4. The method of claim 1, wherein concurrently treating the subject with the immunotherapy comprises administering an immune stimulant with at least one dose of radiation.

5. The method of claim 4, wherein the immune stimulant comprises at least one of a checkpoint inhibitor, an immune stimulating cytokine, a tumor derived immune stimulant, or an agent associated with a cGAS STING pathway.

6. The method of claim 1, further comprising training the machine learning model to analyze radiomic features and biologic features.

7. The method of claim 6, wherein the biologic features comprise at least one of target tissue vascularity, normal tissue vascularity, target tissue oxygenation status, normal tissue oxygenation status, target tissue cytokine profile, normal tissue cytokine profile, target tissue gene expression, normal tissue gene expression, circulating tumor DNA indicative of tumor response to therapy, levels of circulating tumor cells, target tissue receptor expression, normal tissue receptor expression, target tissue white blood cell infiltration, normal tissue white blood cell infiltration, tumor markers, tumor burden, systemic immune status, changes in subject health, or changes in patient weight.

8. The method of claim 6, wherein the radiomic features comprise at least one of anatomical imaging characteristics, functional imaging characteristics, or metabolic imaging characteristics.

9. The method of claim 1, wherein the tumor is one of a benign tumor and a malignant tumor.

10. The method of claim 1, wherein the first pulse dose is at least 6 Gy.

11. The method of claim 1, wherein the second pulse dose is between 15 Gy and 50 Gy.

12. A method of adaptive treatment of a subject with a tumor comprising:

administering a first pulse dose of radiation to the tumor within the subject;

concurrently treating the subject with an immunotherapy;

measuring biologic features of at least one of the subject or the tumor;

applying at least one medical imaging technique to at least one of the subject or the tumor;

analyzing results of the at least one medical imaging technique and the biologic features with a machine learning model;

determining, based on the analysis with the machine learning model, at least a duration between the first pulse dose and a second pulse dose; and administering the second pulse dose, wherein the second pulse dose is administered at least 7 days after the first pulse dose.

13. The method of claim 12, wherein the first and second pulse doses of radiation are ablative.

14. The method of claim 12, wherein the biologic features comprise at least one of target tissue vascularity, normal tissue vascularity, target tissue oxygenation status, normal tissue oxygenation status, target tissue cytokine profile, normal tissue cytokine profile, target tissue gene expression, normal tissue gene expression, circulating tumor DNA indicative of tumor response to therapy, levels of circulating tumor cells target tissue receptor expression, normal tissue receptor expression, target tissue white blood cell infiltration, normal tissue white blood cell infiltration, tumor markers, tumor burden, systemic immune status, changes in subject health, or changes in patient weight.

15. The method of claim 12, wherein the at least one medical imaging technique comprises at least one of anatomical imaging, functional imaging, or metabolic imaging.

16. The method of claim 12, wherein concurrently treating the subject with the immunotherapy comprises administering an immune stimulant with at least one of the first pulse dose or the second pulse dose of radiation.

17. The method of claim 16, wherein the immune stimulant comprises a checkpoint inhibitor, an immune stimulating cytokine, a tumor derived immune stimulant, or an agent associated with a cGAS STING pathway.

18. The method of claim 12, wherein the first and second pulse doses are part of a radiotherapy, the radiotherapy comprising stereotactic ablative radiotherapy (SABR).

19. A method of adaptive treatment of a subject with a tumor comprising:

administering a first pulse dose of radiation to the tumor within the subject;

measuring biologic features of at least one of the subject or the tumor;

applying at least one medical imaging technique to at least one of the subject or the tumor;

analyzing results of the at least one medical imaging technique and the biologic features with a machine learning model;

determining, based on the analysis with the machine learning model, at least a duration between the first pulse dose and a second pulse dose; and administering the second pulse dose, wherein the second pulse dose is administered at least 7 days after the first pulse dose.

* * * * *